(12) United States Patent
Hartounian et al.

(10) Patent No.: US 9,585,838 B2
(45) Date of Patent: *Mar. 7, 2017

(54) PRODUCTION OF MULTIVESICULAR LIPOSOMES

(75) Inventors: Hartoun Hartounian, San Diego, CA (US); Dagmar Meissner, Cardiff, CA (US); Clint B. Pepper, Oceanside, CA (US)

(73) Assignee: Pacira Pharmaceuticals, Inc., San Diego, CA (US)

( * ) Notice: Subject to any disclaimer, the term of this patent is extended or adjusted under 35 U.S.C. 154(b) by 1137 days.

This patent is subject to a terminal disclaimer.

(21) Appl. No.: 11/678,615

(22) Filed: Feb. 25, 2007

(65) Prior Publication Data

US 2007/0235889 A1 Oct. 11, 2007

Related U.S. Application Data

(63) Continuation of application No. 09/192,064, filed on Nov. 13, 1998, now abandoned.

(60) Provisional application No. 60/065,856, filed on Nov. 14, 1997.

(51) Int. Cl.
| | |
|---|---|
| *A61K 9/127* | (2006.01) |
| *A61K 31/439* | (2006.01) |
| *A61K 31/7036* | (2006.01) |
| *A61K 31/7068* | (2006.01) |
| *A61K 38/30* | (2006.01) |

(52) U.S. Cl.
CPC ............ *A61K 9/127* (2013.01); *A61K 9/1277* (2013.01); *A61K 31/439* (2013.01); *A61K 31/7036* (2013.01); *A61K 31/7068* (2013.01); *A61K 38/30* (2013.01)

(58) Field of Classification Search
CPC ... A61K 9/127; A61K 9/1271; A61K 9/12717
USPC .............................. 424/450; 264/4.1, 4.3, 4.6
See application file for complete search history.

(56) References Cited

U.S. PATENT DOCUMENTS

| | | |
|---|---|---|
| 3,684,251 A | 8/1972 | Bowling |
| 3,946,994 A | 3/1976 | Mertz et al. |
| 4,026,817 A | 5/1977 | Ciuti et al. |
| 4,078,052 A | 3/1978 | Papahadjopoulos |
| 4,089,801 A | 5/1978 | Schneider |
| 4,113,765 A | 9/1978 | Richardson et al. |
| 4,145,410 A | 3/1979 | Sears |
| 4,224,179 A | 9/1980 | Schneider |
| 4,235,587 A | 11/1980 | Miles |
| 4,235,871 A | 11/1980 | Papahadjopoulos et al. |
| 4,310,506 A | 1/1982 | Baldeschwieler et al. |
| 4,394,372 A | 7/1983 | Taylor |
| 4,420,398 A | 12/1983 | Castino |
| 4,454,083 A | 6/1984 | Brown et al. |
| 4,478,824 A | 10/1984 | Franco et al. |
| 4,522,803 A | 6/1985 | Lenk et al. |
| 4,588,578 A | 5/1986 | Fountain et al. |
| 4,590,030 A | 5/1986 | Gillner et al. |
| 4,599,227 A | 7/1986 | Dees et al. |
| 4,599,342 A | 7/1986 | La Hann |
| 4,610,868 A | 9/1986 | Fountain et al. |
| 4,622,219 A | 11/1986 | Haynes |
| 4,644,056 A | 2/1987 | Kothe et al. |
| 4,652,441 A | 3/1987 | Okada et al. |
| 4,668,580 A | 5/1987 | Dahm et al. |
| 4,711,782 A | 12/1987 | Okada et al. |
| 4,725,442 A | 2/1988 | Haynes |
| 4,744,989 A | 5/1988 | Payne et al. |
| 4,752,425 A | 6/1988 | Martin et al. |
| 4,761,255 A | 8/1988 | Dahm et al. |
| 4,761,288 A | 8/1988 | Mezei |
| 4,769,250 A | 9/1988 | Forssen |
| 4,776,991 A | 10/1988 | Farmer et al. |
| 4,781,831 A * | 11/1988 | Goldsmith .................... 210/247 |
| 4,781,871 A | 11/1988 | West, III et al. |
| 4,788,001 A | 11/1988 | Narula |
| 4,844,620 A | 7/1989 | Lissant et al. |
| 4,844,904 A | 7/1989 | Hamaguchi et al. |
| 4,861,597 A | 8/1989 | Kida et al. |
| 4,877,561 A | 10/1989 | Iga et al. |
| 4,877,619 A | 10/1989 | Richer |
| 4,908,463 A | 3/1990 | Bottelberghe |
| 4,920,016 A | 4/1990 | Allen et al. |
| 4,921,853 A | 5/1990 | LeBlanc |
| 4,937,078 A | 6/1990 | Mezei et al. |
| 4,956,290 A * | 9/1990 | Harrison et al. .............. 435/189 |
| 5,000,959 A | 3/1991 | Iga et al. |
| 5,004,611 A | 4/1991 | Leigh |
| 5,013,556 A | 5/1991 | Woodle et al. |
| 5,019,394 A | 5/1991 | Hamaguchi et al. |
| 5,021,200 A | 6/1991 | Vanlerberghe et al. |
| 5,049,392 A | 9/1991 | Weiner et al. |
| 5,069,936 A | 12/1991 | Yen |
| 5,077,056 A | 12/1991 | Bally et al. |
| 5,091,187 A | 2/1992 | Haynes |
| 5,094,854 A | 3/1992 | Ogawa et al. |
| 5,100,591 A | 3/1992 | Leclef et al. |

(Continued)

FOREIGN PATENT DOCUMENTS

| | | |
|---|---|---|
| CA | 1323568 | 8/1988 |
| CA | 2 078 666 | 10/1991 |

(Continued)

OTHER PUBLICATIONS

Roy et al., Cancer Chemother Pharmacol, 28:105-108 (1991).

(Continued)

*Primary Examiner* — Gollamudi Kishore
(74) *Attorney, Agent, or Firm* — Knobbe Martens Olson & Bear LLP

(57) ABSTRACT

Multivesicular liposomes are prepared at commercial scales by combining a first w/o emulsion with a second aqueous solution to form a w/o/w emulsion using a static mixer. Solvent is removed from the resulting emulsion to form multivesicular liposome-containing compositions. Further optional process steps include primary filtration and secondary cross-flow filtration. The products produced according to the processes of the invention can be produced through a series of aseptic steps.

43 Claims, 15 Drawing Sheets

(56) References Cited

U.S. PATENT DOCUMENTS

| | | |
|---|---|---|
| 5,141,674 A | 8/1992 | Leigh |
| 5,147,134 A | 9/1992 | Bradley et al. |
| 5,169,637 A | 12/1992 | Lenk et al. |
| 5,186,941 A | 2/1993 | Callahan et al. |
| 5,192,549 A | 3/1993 | Barenolz et al. |
| 5,204,112 A | 4/1993 | Hope et al. |
| 5,211,955 A | 5/1993 | Legros et al. |
| 5,225,212 A | 7/1993 | Martin et al. |
| 5,227,165 A | 7/1993 | Domb et al. |
| 5,227,170 A | 7/1993 | Sullivan |
| 5,244,678 A | 9/1993 | Legros et al. |
| 5,246,707 A | 9/1993 | Haynes |
| 5,261,903 A | 11/1993 | Dhaliwal et al. |
| 5,292,701 A * | 3/1994 | Glemza et al. ............. 502/202 |
| 5,321,012 A | 6/1994 | Mayer et al. |
| 5,334,381 A | 8/1994 | Unger |
| 5,334,391 A | 8/1994 | Clark et al. |
| 5,364,632 A | 11/1994 | Benita et al. |
| 5,387,387 A * | 2/1995 | James et al. ................. 264/205 |
| 5,393,530 A | 2/1995 | Schneider et al. |
| 5,407,660 A | 4/1995 | Bosworth et al. |
| 5,415,867 A * | 5/1995 | Minchey et al. ............ 424/450 |
| 5,422,120 A | 6/1995 | Kim |
| 5,451,408 A | 9/1995 | Mezei et al. |
| 5,455,044 A | 10/1995 | Kim et al. |
| RE35,192 E | 3/1996 | Reese |
| 5,543,158 A | 8/1996 | Gref et al. |
| 5,576,017 A | 11/1996 | Kim |
| 5,576,018 A | 11/1996 | Kim et al. |
| 5,589,189 A | 12/1996 | Moynihan |
| 5,635,205 A | 6/1997 | Nyvist et al. |
| 5,658,898 A | 8/1997 | Weder et al. |
| 5,662,931 A | 9/1997 | Munechika et al. |
| 5,681,464 A * | 10/1997 | Larsson .................. 210/321.84 |
| 5,700,482 A | 12/1997 | Frederiksen et al. |
| 5,708,011 A | 1/1998 | Bardsley et al. |
| 5,723,147 A | 3/1998 | Kim et al. |
| 5,766,627 A | 6/1998 | Sankaram et al. |
| 5,770,222 A | 6/1998 | Unger et al. |
| 5,776,486 A | 7/1998 | Castor et al. |
| 5,776,915 A * | 7/1998 | Peterson et al. ................ 514/77 |
| 5,807,573 A | 9/1998 | Ljusberg-Wahren et al. |
| 5,814,335 A | 9/1998 | Webb et al. |
| 5,827,533 A | 10/1998 | Needham |
| 5,837,282 A | 11/1998 | Fenske et al. |
| 5,849,763 A | 12/1998 | Bardsley et al. |
| 5,853,755 A | 12/1998 | Foldvari |
| 5,865,184 A | 2/1999 | Takiguchi |
| 5,879,672 A * | 3/1999 | Davis et al. ................. 424/85.1 |
| 5,882,679 A | 3/1999 | Needham |
| 5,885,260 A | 3/1999 | Mehl, Sr. et al. |
| 5,891,467 A | 4/1999 | Willis |
| 5,891,842 A | 4/1999 | Kream |
| 5,895,661 A | 4/1999 | Tournier et al. |
| 5,910,502 A | 6/1999 | Gennery |
| 5,912,271 A | 6/1999 | Brodin et al. |
| 5,919,804 A | 7/1999 | Gennery |
| 5,922,340 A | 7/1999 | Berde et al. |
| 5,942,253 A | 8/1999 | Gombotz et al. |
| 5,945,126 A | 8/1999 | Thanoo et al. |
| 5,945,435 A | 8/1999 | Evetts |
| 5,947,689 A | 9/1999 | Schick |
| 5,948,441 A | 9/1999 | Lenk et al. |
| 5,955,087 A * | 9/1999 | Whittle et al. ............. 424/204.1 |
| 5,955,479 A | 9/1999 | Bardsley et al. |
| 5,962,016 A | 10/1999 | Willis |
| 5,962,532 A | 10/1999 | Campbell et al. |
| 5,977,326 A | 11/1999 | Scheinmann et al. |
| 5,980,927 A | 11/1999 | Nelson et al. |
| 5,980,937 A * | 11/1999 | Tournier et al. ............. 424/450 |
| 5,997,899 A | 12/1999 | Ye et al. |
| 6,007,838 A * | 12/1999 | Alving et al. ................ 424/450 |
| 6,033,708 A | 3/2000 | Kwasiborski et al. |
| 6,045,824 A | 4/2000 | Kim et al. |
| 6,046,187 A | 4/2000 | Berde |
| 6,048,545 A | 4/2000 | Keller et al. |
| 6,066,331 A | 5/2000 | Barenholz et al. |
| 6,069,155 A | 5/2000 | Mather et al. |
| 6,071,534 A | 6/2000 | Kim et al. |
| 6,103,741 A | 8/2000 | Bardsley et al. |
| 6,106,858 A | 8/2000 | Ye et al. |
| 6,120,797 A | 9/2000 | Meers et al. |
| 6,132,766 A | 10/2000 | Sankaram et al. |
| 6,149,937 A | 11/2000 | Camu et al. |
| 6,171,613 B1 | 1/2001 | Ye et al. |
| 6,193,998 B1 | 2/2001 | Ye et al. |
| 6,217,899 B1 * | 4/2001 | Benameur et al. ........... 424/450 |
| 6,221,401 B1 | 4/2001 | Zasadzinski et al. |
| 6,238,702 B1 | 5/2001 | Berde et al. |
| 6,241,999 B1 | 6/2001 | Ye et al. |
| 6,264,988 B1 | 7/2001 | Yen |
| 6,270,802 B1 | 8/2001 | Thanoo et al. |
| 6,287,587 B2 | 9/2001 | Shigeyuki et al. |
| 6,306,432 B1 | 10/2001 | Shirley et al. |
| 6,355,267 B1 * | 3/2002 | Collins ........................ 424/450 |
| 6,399,094 B1 | 6/2002 | Brandl et al. |
| 6,417,201 B1 | 7/2002 | Bardsley et al. |
| 8,182,835 B2 | 5/2012 | Kim et al. |
| 2002/0041895 A1 | 4/2002 | Gregoriadis |

FOREIGN PATENT DOCUMENTS

| | | |
|---|---|---|
| CA | 078666 | 10/1991 |
| CA | 1 337 273 | 10/1995 |
| CA | 2199004 | 11/1999 |
| EP | 0126580 A2 | 11/1984 |
| EP | 0 208 450 | 1/1987 |
| EP | 0280503 A2 | 8/1988 |
| EP | 0506639 | 3/1992 |
| EP | 0 752 245 | 1/1997 |
| GB | 2050287 | 1/1981 |
| JP | 61-27918 | 5/1994 |
| WO | WO 85/03011 | 7/1985 |
| WO | WO 89/00846 | 2/1989 |
| WO | WO 89/04656 | 6/1989 |
| WO | WO 91/014445 | 10/1991 |
| WO | WO 93/00888 | 1/1993 |
| WO | WO 94/08626 | 4/1994 |
| WO | PCT/US94/04490 | 7/1994 |
| WO | WO 94/22430 | 10/1994 |
| WO | WO 94/023697 | 10/1994 |
| WO | WO 94/026250 | 11/1994 |
| WO | WO 94/27581 | 12/1994 |
| WO | WO 95/01164 | 1/1995 |
| WO | WO 95/13796 | 5/1995 |
| WO | WO 96/08235 | 3/1996 |
| WO | WO 96/14057 | 5/1996 |
| WO | PCT/US96/11642 | 9/1996 |
| WO | WO 97/02022 | 1/1997 |
| WO | WO 97/003652 | 2/1997 |
| WO | WO 97/35561 | 10/1997 |
| WO | WO 98/014171 | 4/1998 |
| WO | WO 98/033483 | 8/1998 |

OTHER PUBLICATIONS

Turski et al., Magnetic Resonance in Medicine, 2(7):184-196 (1998).
Skuta et al., Am J Ophth, 5(103):714-716 (1987).
Barbet et al., Biochimica Biophysica Acta, 3(772):347-356 (1984).
Kim et al., Biochim Biophys Acta, 646:1-9 (1981).
Kim et al., Biochim Biophys Acta, 728:339-48 (1983).
Kim et al., Biochim Biophys Acta, 812:793-801 (1985).
Kim et al., Cancer Res, 47:3935-37 (1987).
Kim et al., Cancer Treat Rep, 71:447-50 (1987).
Kim et al., Cancer Chemother Pharmacol, 19:307-10 (1987).
Assil, "Multivesicular Liposomes. Sustained release of the antimetabolit . . . ;" Arch Ophthal, 3(105):400 (1987).
Kim, "Multivesicular Liposomes Containing Cytarabine Entrapped in the Presence of . . . ," Cancer Treatment Reports, 71:705-11 (1987).

(56) References Cited

OTHER PUBLICATIONS

Bonetti, "An extended release formulation of methotrexate . . . ," Cancer Chemother Pharmacol, In Press (1994).
Matsumoto et al., "An attempt at preparing water-in-oil multiple-phase emulsions . . . ," J Colloid Interface Sci, 57(2):353-61 (1976).
Saberi et al., "Bubble size and velocity measurement in gas-liquid systems . . . ," Can J Chem Eng, 73(April):253-7 (1995).
Tsuchiya et al., "Tortuosity of bubble rise path in a liquid-solid fluidized bed . . . ," AIChE Journal, 41(6):1368-74 (1995).
Chattopadhyay et al., "The protective effect of specific medium additives . . . ," Biotech Bioeng, 45:473-80 (1995).
Cherry et al., "Cell death in the thin films of bursting bubbles," Biotechnology, 8(1):11-18 (1992).
Michaels et al., "Sparing and agitation-induced injury of cultured animal cells . . . ," Biotech and Bioeng, 51:399-409 (1996).
Andrews et al., "Boundary layer solution for a bubble rising through a liquid . . . ," Ind Eng Chem Res, 34(4):1371-82 (1995).
Arroyo et al., "Use of intermittent jets to enhance flux in crossflow filtration," J Membrane Sci, 80:117-29 (1993).
Jaffrin et al., "Energy saving pulsatile mode cross flow filtration," J Membrane Sci, 86:281-90 (1993).
Maranges et al., "Crossflow filtration of *Saccharomyces cerevisiae* using an unsteady jet," Biotech Techniques, 9(9):649-54 (1995).
Maa et al., "Liquid-liquid emulsification by rotor/stator homogenization," J Controlled Release, 38(2,3):219-28 (1996).
Holdich et al., "The variation of crossflow filtration rate with wall shear stress and the effect . . . ," Chem Eng Res Design, 73(A1):20-26 (1995).
Huang, Biochemistry, 8:334-352 (1969).
Bangham, J Mol Bio, 13:238-52 (1965).
Szoka et al., Ann Rev Biophys Bioengineering, 9:467-508 (1980) 1111.
Shakiba et al., Investigative Ophth Visual Sci, 10(34):2891-97 (1993).
Frucht-Perry et al., Cornea, 5(11):393-397 (1992).
Kawashima et al., "Shear-induced phase inversion and size control of water/oil/water . . . ," J Colloid Interface Sci, 145(2):512-23 (1991).
Watts et al., "Microencapsulation using emulsification/solvent evaportaion . . . ," Crit Rev Therap Drug Carrier Sys, 7(3):235-59 (1990).
Mancini, "Mastering the mix . . . ," Food Engineering, Mar. 1996 pp. 79-83.
Mutsakis et al., "Advances in static mixing technology," Chem Eng Progress, Jul. 1986 pp. 42-48.
Steiff et al., "Don't overlook static mixer reactors," Chem Eng, 1(6):76-82 (1994).
Kim, T. et al., "Extended-release formulations of morphine for subcutaneous administration," Cancer Chemother Pharmacol, 33:187-90 (1993).
Johnson et al., Oil and Gas Journal, 92(43):80-86 (1994).
Tanaka et al., "Crossflow filtration of Baker's yeast with periodical stopping . . . ," Biotech Bioeng, 47(3):401-404 (1995).
Rodgers et al., "Reduction of membrane fouling in the ultrafiltration of binary . . . ," AIChE Journal, 37(10):1517-28.
Redkar et al., "Crossflow microfiltration with high frequency reverse filtration," AIChE Journal, 41(3):501-508.
Kim et al., Cancer Res, 53:1596-98 (1993).
Kim et al., J Infectious Diseases, 162:750-52 (1990).
Chamberlain et al., Arch Neurol, 50:261-264 (1993).
Chatelut et al., Cancer Chemother Pharmacol, 32:179-182 (1993).
Russack et al., Ann Neural, 34:108-112 (1993).
Kim et al., J Cm Oncol, 11:2186-2193 (1993).
Kim et al., Drugs, 46(4):618-38 (1993).
Ishii, Liposome Technology, 1:111-121 (1993).
Cullis et al., Phospholipids and Cellular Regulation, 1:65-123 (1985).
Gruner et al., Biochemistry, 24(12):2833-42 (1985).
Narhi et al., Biochemistry, 19:5214-21 (1993).
Kim et al., Biochimica Biophysica Acta, 728:339-48 (1983).

Edwards et al., Science, 276:1868-71 (1997).
Assil et al., Investig Ophth and Visual Sci, 32(13):2891-97 (1991).
Paul, "Reaction systems for bulk pharmaceutical production," Chemistry & Industry, 10:320-25 (1990).
Australian Examiner's First Report mailed on Feb. 12, 2010 in Australian Patent Application No. 2008203032, filed Nov. 13, 1998.
Australian Examiner's First Report mailed on Jul. 11, 2001 in Australian Patent Application No. 14075/99, filed Nov. 13, 1998.
Australian Examiner's Second Report mailed on Dec. 5, 2001 in Australian Patent Application No. 14075/99, filed Nov. 13, 1998.
Australian Examiner's First Report mailed on Oct. 9, 2006 in Australian Patent Application No. 2006200044, filed Nov. 13, 1998.
Australian Examiner's First Report mailed on Jul. 6, 2004 in Australian Patent Application No. 2002301268, filed Nov. 13, 1998.
Japanese Office Action mailed on May 26, 2009 in Japanese Patent Application No. 2000-520753, filed Nov. 13, 1998.
Japanese Final Office Action mailed on Jan. 19, 2010 in Japanese Patent Application No. 2000-520753 filed Nov. 13, 1998.
European Official Communication mailed on Oct. 18, 2010 in European Patent Application No. 98957937.0, filed Nov. 13, 1998.
European Official Communication mailed on Dec. 18, 2008 in European Patent Application No. 98957937.0, filed Nov. 13, 1998.
European Official Communication mailed on Jan. 28, 2008 in European Patent Application No. 98957937.0, filed Nov. 13, 1998.
European Official Communication mailed on May 10, 2007 in European Patent Application No. 98957937.0, filed Nov. 13, 1998.
European Supplemental European Search Report mailed on Apr. 6, 2006 in European Patent Application No. 98957937.0, filed Nov. 13, 1998.
Genovesi, "Several uses for tangential-flow filtration in the pharmaceutical industry," *J. Parenter. Sci. Technol.* (1983), 37(3):81-86.
"Guidance for Industry: Guideline on Sterile Drug Products Produced by Aseptic Processing," Jun. 1987, Reprinted Jun. 1991, pp. 1-43, Center for Drug Evaluation and Research et al.
Quirk et al., "Investigation of the parameters affecting the separation of bacterial enzymes from cell debris by tangential flow filtration," *Enzyme Microb. Technol.* (1984), 6(5):201-206.
Radlett, "The Concentration of Mammalian Cells in a Tangential Flow Filtration Unit," *J. Appl. Chem. Biotechnol.* (1972), 22:495-499.
Bhave, "Cross-Flow Filtration," Fermentation and Biochemical Engineering Handbook: Principles, Process Design and Equipment, $2^{nd}$ edition, (Vogel et al. Eds., 1997), Noyes Publications, Westwood, New Jersey, pp. 271-278.
Australian Examiner's First Report mailed on Feb. 8, 2013 in Australian Patent Application No. 2012203661, filed Jun. 22, 2012.
Canadian Office Action mailed on Dec. 9, 2003 in Canadian Patent Application No. 2309548.
Canadian Office Action mailed on Jan. 6, 2005 in Canadian Patent Application No. 2309548.
Canadian Office Action mailed on Jan. 26, 2006 in Canadian Patent Application No. 2309548.
Japanese Office Action mailed on Nov. 13, 2012 in Japanese Patent Application No. 2010-162514, filed Nov. 13, 1998.
Japanese Office Action mailed on Sep. 3, 2013 in Japanese Patent Application No. 2010-162514, filed Nov. 13, 1998.
PCT International Preliminary Examination Report mailed on Jan. 20, 2000 in PCT Application No. PCT/US98/24261, filed Nov. 13, 1998.
PCT Written Opinion mailed Sep. 21, 1999 in PCT Application No. PCT/US98/24261, filed Nov. 13, 1998.
PCT International Search Report mailed Jan. 25, 1999 in PCT Application No. PCT/US98/24261, filed Nov. 13, 1998.
De Gier, J et al., Lipid Composition and Permeability of Liposomes, Biochim. Biophys. Acta 150:666-675 (1968).
Meissner, D., et al., Application of High Frequency Backpulsing in Diafiltration of Multivesicular Liposomes, North American Membrane Society, Proceedings, $9^{th}$ Annual Meeting, May 31-Jun. 4 1997, Baltimore, MD, (1997). Abstract.
Meissner, D., et al., Application of Unsteady Flow Patterns in Permeate and Retentate for the Diafiltration of Multivesicular Lipid

(56) References Cited

OTHER PUBLICATIONS

Based Particles, Annual AIChE Meeting, Nov. 16-21 1997, Los Angeles, CA. Unpublished conference paper (1997). Linda Hall Library, Kansas.
Thompson, G.A. Jr., The Regulation of Membrane Lipid Metabolism $2^{nd}$ Ed., CRC Press: Boca Raton, pp. 1-20 (1992).

* cited by examiner

PRODUCTION OF MULTIVESICULAR LIPOSOMES

CROSS REFERENCE TO RELATED APPLICATIONS

This application claims priority from U.S. application Ser. No. 09/192,064, filed on Nov. 13, 1998, which claims priority from U.S. Provisional Patent Application Ser. No. 60/065,856, filed on Nov. 14, 1997, incorporated herein by reference.

BACKGROUND OF THE INVENTION

This invention relates generally to the field of methods of encapsulation of physiologically active substances. More specifically, the invention relates to emulsification processes for preparing multivesicular liposome formulations, with sustained release characteristics and the formulations produced by those processes.

When phospholipids and many other amphipathic lipids are dispersed gently in an aqueous medium they swell, hydrate, and spontaneously form multilamellar concentric bilayer vesicles with layers of aqueous media separating the lipid bilayers. These systems are commonly referred to as multilamellar liposomes or multilamellar vesicles (MLV), and usually have diameters of from 0.2 to 5 µm. Sonication of MLV results in the formation of small unilamellar vesicles (SUV) containing an aqueous solution, bounded by a single lipid bilayer with diameters usually in the range of from 20 to 100 nm. Multivesicular liposomes (MVL) differ from MLV and SUV in the way they are manufactured, in the random, non-concentric arrangement of aqueous-containing chambers within the liposome, and in the inclusion of neutral lipids necessary to form the MVL.

Various types of lipids differing in chain length, saturation, and head group have been used for years in liposomal drug formulations, including the unilamellar, multilamellar, and multivesicular liposomes mentioned above. The neutral lipids used in the manufacture of multivesicular liposomes to date have been primarily limited to triglycerides.

Liposomes in various forms have been prepared by a variety of different processes. However, most such processes are suitable only for laboratory-scale preparation, and are not readily scaled up to batch sizes suitable for commercial production. Thus, a need exists for liposome preparation processes that are suitable for large-scale manufacturing. Among the challenges for the design of an efficient and effective large-scale manufacturing process for (multivesicular) liposomes is the need to bring together unit operations in an efficient manner. Such unit operations include: 1) first emulsification, 2) second emulsification, 3) solvent removal, 4) primary filtration and other ancillary operations necessary for the large-scale production of MVL. The process can also be carried out in an aseptic manner, and such processes are considered desirable.

The rheology of water-in-oil (w/o) emulsions, and specifically the effects of volume fraction and size on viscosity, have been well studied in literature. Multiple emulsion processes are currently used in the pharmaceutical industry to obtain sustained-release drug products. These processes in general begin with the formation of a emulsion with a high volume fraction of dispersed phase (0.6-0.85). High-shear mixing is generally used to obtain a emulsion of high viscosity (from 5-100 times that of the continuous phase) that is stable enough to be further processed.

It is known that the shearing of emulsions in a batch reactor will result in a decrease in the size of droplets in the emulsion. When the shear forces of the mixer exceed the surface tension on discontinuous phase droplets, these forces act to break up the droplets and reduce the mean droplet size. This reduction of droplet size has significant effects on the rheology of the emulsion, with emulsions of smaller droplet size having a higher viscosity. The increase in viscosity with increased mixing time and speed is due to two principle factors. First, smaller droplets have a higher surface tension and are more rigid, resulting in an emulsion with higher viscosity. Second, a decrease in droplet size decreases the mean separation distance between the droplets, resulting in increased hydrodynamic interactions between droplets. The effect of droplet size on emulsion viscosity is magnified as droplet size decreases.

After the w/o emulsion has been formed and it is no longer undergoing any shear forces, many interactions are still occurring within the emulsion. In concentrated dispersions, Brownian motion comes into play, especially if droplet size is small. As Brownian motion causes the droplets to become randomized, collisions between droplets increase and aggregates are formed. In addition, if a w/o emulsion consists of lipids with monolayer membranes of the droplets having their hydrophobic chains facing away from the droplets, attractive hydrophobic interactions occur between droplets, that promote formation of aggregates. When the viscosity of an emulsion containing aggregates is measured at low shear rates, the viscosity is high, while at higher shear rates the aggregates are broken, and the viscosity decreases. Thus, w/o emulsions are shear thinning.

Water in oil in water (w/o/w) emulsions have been prepared by dispersing w/o emulsions into a second aqueous phase. Removal of the solvent of the oil phase by various techniques results in encapsulated materials, present in a second aqueous phase. These materials have found applications in foods, cosmetics, treatment of waste water, and pharmaceuticals.

The removal of solvent from the oil phase to produce such encapsulated materials has been carried out by passing inert gas through the w/o/w emulsion. It has been observed that conventional techniques can result in damage to the encapsulated materials, leading to rupture and loss of material into the second aqueous phase. After the solvent removal step, the encapsulated materials need to be subjected to a primary filtration step.

The primary filtration step has several objectives: exchange the second aqueous solution by a physiologically acceptable solution, concentration adjustment of the multivesicular lipid based particles, and removal of unencapsulated drug. The primary strategy of the prior art for maximizing diafiltration productivity in the manufacture of lipid based particles is to reduce fouling and gel polarization of the membrane. Basic process parameters such as wall shear rate, permeate flux, and transmembrane pressure can be optimized in order to achieve this goal. However, the success of these optimization efforts is limited since the permeate flux drops significantly during the primary filtration process.

In the manufacture of multivesicular liposomes encapsulating various drugs and other active agents, the diafiltration process consumes approximately 60% of the actual process time. Therefore, it is an economical consideration to reduce the time of the diafiltration process to reduce operating cost without compromising the product quality. The approach used in conventional cross-flow systems for reducing the processing time by increasing the wall shear rate or the membrane surface area is counterproductive because multivesicular liposomes are shear sensitive. Increasing the shear rate and membrane surface area, which in turn requires use of a larger pump, results in damaging the particles and reducing the encapsulating yield.

Another concentration adjustment step is often necessary after primary filtration, since the holdup of primary filtration is too great to allow adjustment in one step. Historically, decanting the primary filtration product has been used, although a number of difficulties arise with this approach. Sterility breach is a problem, as well as the necessity of allowing a long resettling time after such a procedure. Concentration adjustment by this method is time-consuming and not particularly accurate.

The products must be sterile for use in human and in many other organisms. Conventional terminal sterilization techniques such as autoclaving and gamma irradiation can damage delicate products, including MVL.

Therefore, due to these problems, new and better methods are required for reducing the process time and shear stress on lipid particles, such as multivesicular particles, during diafiltration. Methods are also required which can reliably produce sterile product without undue product damage.

SUMMARY OF THE INVENTION

A new process for preparing MVLs has been invented. This process is suitable for manufacturing at commercial scales. The MVL can be produced aseptically, or can be subjected to non-destructive terminal sterilization.

In one aspect, the invention provides a process for producing MVL by providing a water in oil (w/o) emulsion, which is made from an aqueous phase dispersed in a solvent phase containing amphipathic and neutral lipids. Amphipathic lipids can be chosen from a large group including phosphatidylcholines, phosphatidylethanolamines, sphingomyelins, lysophosphatidylcholines, lysophosphatidylethanolamines, are phosphatidylglycerols, phosphatidylserines, phosphatidylinositols, phosphatidic acids, cardiolipins, acyl trimethylammonium propane, diacyl dimethylammonium propane, stearylamine, and ethyl phosphatidylcholine. Neutral lipids can be selected from glycerol esters, glycol esters, tocopherol esters, sterol esters, alkanes and squalenes. Physiologically active substances can be included in either the aqueous or solvent phase, and are chosen from a wide range of materials including antianginas, antiarrhythmics, antiasthmatic agents, antibiotics, antidiabetics, antifungals, antihistamines, antihypertensives, antiparasitics, antineoplastics, antitumor drugs, antivirals, cardiac glycosides, hormones, immunomodulators, monoclonal antibodies, neurotransmitters, nucleic acids, proteins, radio contrast agents, radionuclides, sedatives, analgesics, steroids, tranquilizers, vaccines, vasopressors, anesthetics, peptides, prodrugs and pharmaceutically acceptable salts of these materials. Specific materials such as cytarabine, insulin, paclitaxel, 5-fluorouracil, floxuridine, morphine, hydromorphine, dexamethasone, methotrexate, bleomycin, vincristine, vinblastine, IgF-1, bupivacaine and amikacin can be included.

In another aspect, the invention provides a way to accurately and quickly scale up reactions at least 10 fold. An initial emulsion (which can be 0.2 to 40 liters) is prepared in a mixer, and considering the blade speed and measured viscosity, the emulsion can be scaled up to produce an emulsion with the same particle size.

The w/o emulsion is dispersed into another aqueous phase to make water-in-oil-in-water (w/o/w) emulsion. This second aqueous phase can include sugars and amino acids. The solvent is removed, by contacting the w/o/w emulsion with an inert gas flow, for example in several steps with different gas flow rates. The gas flow rates can increase or decrease with time. They can be changed in discrete steps, or by ramps of flow rate changes. The increases can be from 2 to 5 times the initial flow rates, and can be followed by decreases in the flow rate. After solvent removal, MVL are formed.

The steps can be carried out aseptically, or the MVL can be sterilized before package filling is carried out. In either case, an MVL product results which is immediately suitable for administration in a subject. The w/o/w emulsion can be made in a static mixer, such as a Kenics or Koch type mixer. The w/o emulsion and second aqueous phase can be mixed together in such static mixers at linear velocities of 100 to 500 cm/min. The w/o emulsion can be made by mixing aqueous and solvent phases at volume ratios of from 0.33 to 1.6. The w/o emulsion to second aqueous phase volume ratio can vary from 0.05 to 0.5 in the making of the w/o/w emulsion.

Primary filtration of the MVL composition can also be carried out, and can be performed in a series of steps, concentration from 2 to 6 times the initial concentration, buffer exchange until a desired pH, from 5 to 8 is reached, and optionally, another concentration step. Secondary filtration of the MVL composition can also be carried out, as a final concentration step. Filtration steps can be carried out with hollow fiber filters. Filtration steps can be carried out with transmembrane pressures of from 0.1 to 7 psi. Back pulsing of either filtration process can be carried out, including periodic back pulsing occuring every 0.5 to 10 minutes, and can involve from 0.01 to 5% of the system volume. The back pressure can be as high as 10 psi.

A further potency adjustment step can also be carried out, which can either be by decanting or by a further cross-flow filtration. The parameters for such filtration are generally as above, and are chosen to provide the appropriate potencies which may be required for various products.

In another aspect, the invention provides an MVL composition produced by the processes outlined above.

The term "solvent spherule" as used throughout the specification and claims means a microscopic spheroid droplet of water-immiscible solvent (which could be an organic solvent), within which are multiple smaller droplets of aqueous solution. The solvent spherules are suspended and totally immersed in a second aqueous solution. The use of the term "spherule" should not be taken to limit the droplets to strictly, or even substantially spherical shapes. The solvent spherules can take any of a wide variety of shapes.

The term "neutral lipid" means an oil or fat that has no membrane-forming capability by itself and lacks a hydrophilic "head" group.

The term "amphipathic lipid" means a molecule that has a hydrophilic "head" group and hydrophobic "tail" group and has membrane-forming capability. As used herein, amphipathic lipids include those having a net negative charge, a net positive charge, and zwitterionic lipids. The term "zwitterionic lipid" means an amphipathic lipid with a net charge of zero at pH 7.4. The term "anionic lipid" means an amphipathic lipid with a net negative charge at pH 7.4. The term "cationic lipid" means an amphipathic lipid with a net positive charge at pH 7.4.

The term "neutral lipid" includes oils or fats which have no vesicle-forming capability by themselves, and lack a charged or hydrophilic "head" group. Examples of neutral lipids include, but are not limited to, glycerol esters, glycol esters, tocopherol esters, sterol esters which lack a charged or hydrophilic "head" group, and alkanes and squalenes.

As used herein, the "shelf life" of a liposomal formulation is related to the concentration of the unencapsulated substance ("free drug") in a storage solution, for instance normal saline (0.9% sodium chloride), at a storage temperature, for instance at 4° C. Typically, the shelf life is reached when more than 10% of the drug encapsulated at manufacture is found to be "free", that is, unencapsulated.

Throughout the specification, reference is made to different scales, "laboratory scale", "lab scale", or "bench scale", which refers to reactions and processes of scales less than about a liter, such as 0.025 L, or 0.2 L. The term "commercial scale" refers to preparation of product in quantities or batches greater than or approximately equal to about a liter (or about 0.1 L for proteinaceous preparations) up to 100 L, for example 1, 10, 25 or 75 L. The volumes cited refer nominally to the final volume of product ready for packaging. For example, a "1 L scale" process is scaled to produce a final volume of proper dosage which ranges from about 0.7 to about 1.2 L. For example, a "25 L scale" process is scaled to produce a final volume of proper dosage which ranges from about 17.5 to about 30 L. The actual volume is dependent on the particular substance to be encapsulated.

As used herein, the term "plasma-like medium," means a synthetic solution that includes in addition to normal saline, at least some of the protein or lipid constituents of blood plasma or components of other biological fluids, such as cerebro-spinal fluid (CSF), or interstitial fluids. For instance, normal saline containing citrated human plasma or bovine serum albumin (BSA) is an example of a "plasma-like medium" as the term is used herein.

The term "in vivo conditions" means actual injection or emplacement of MVL into an organism, and includes so-called "ex vivo" incubation of MVL in plasma or a plasma-like medium at body temperature (e.g., 37° C. for humans).

The term "static mixer" as used herein refers to a device intended to be placed in line with one or more fluid conduits or pipes, having an internal geometry designed to mix fluid as it passes through the mixer. The static mixer has no moving parts, and in general accomplishes its function by an arrangement of vanes or baffles that cause turbulent flow under proper conditions.

Unless otherwise defined, all technical and scientific terms used herein have the same meaning as commonly understood by one of ordinary skill in the art tow which this invention belongs. Although methods and materials similar or equivalent to those described herein can be used in the practice or testing of the present invention, suitable methods and materials are described below. All publications, patent applications, patents and other references mentioned herein are incorporated by reference in their entirety. In case of conflict, the present specification, including definitions, will control. In addition, the materials, methods, and examples are illustrative only, and not intended to be limiting.

Other features and advantages of the invention will be apparent from the following detailed description, and from the claims.

DETAILED DESCRIPTION

Figure 1:
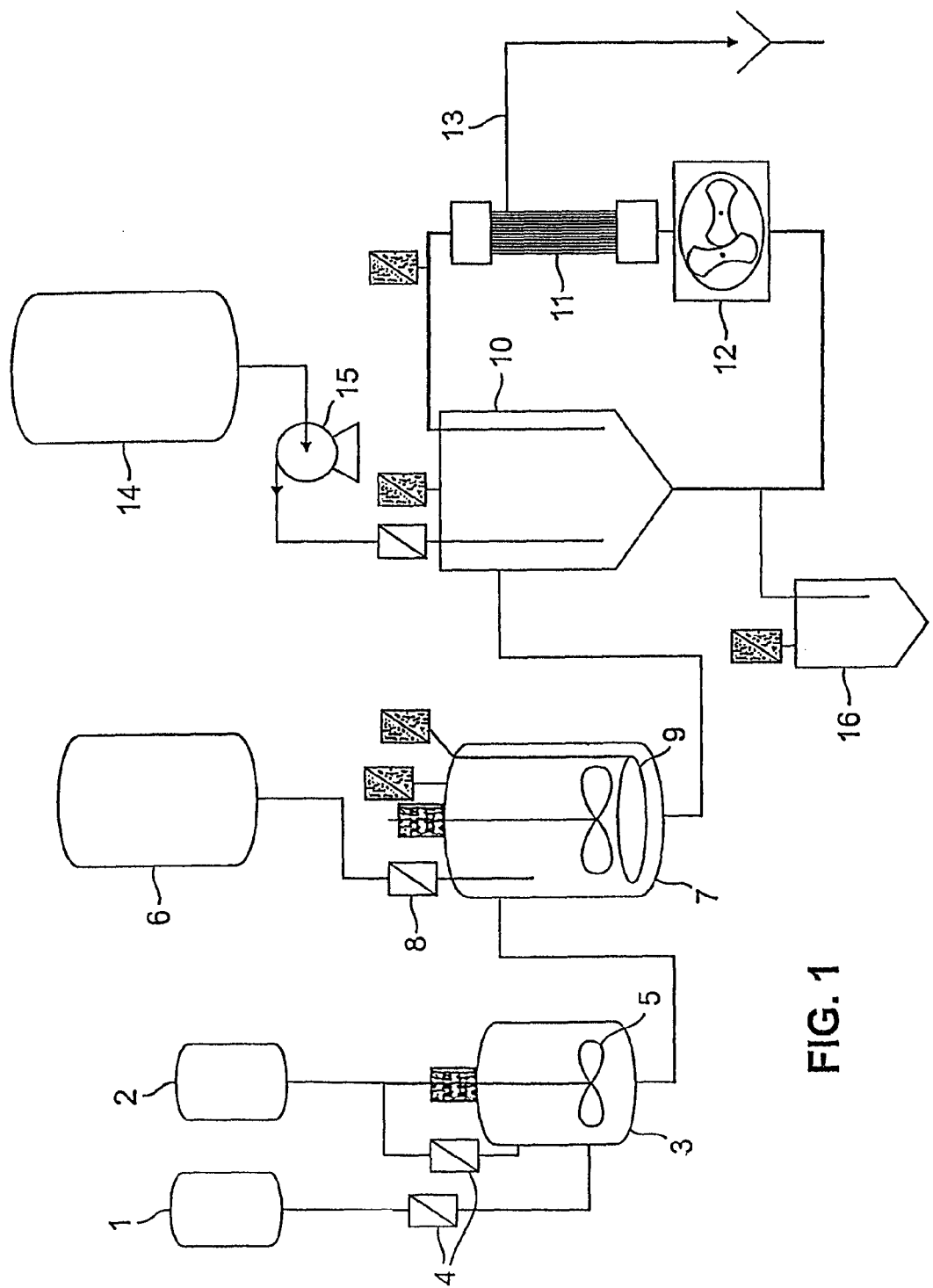
FIG. 1 is a schematic diagram of significant components used in a first particular embodiment of the inventive process.

The invention features a method for producing formulations of multivesicular liposomes (MVL) on a large scale. These MVL can contain physiologically active substances, in which case the MVL provide controlled release of the physiologically active substances. The process provides excellent reproducibility for the MVL with respect to important product specifications. The invention also features methods for the rapid and reproducible scale up of smaller scale processes to large scales.

Production of multivesicular liposomes (MVL) requires several process steps. An example of lab-scale production is set forth in Sankaram et al., U.S. Pat. No. 5,766,627, incorporated herein by reference. Briefly, the method for making MVL at the laboratory scale is as follows: a water-in-oil (w/o) emulsion is prepared by capturing in a lipid component composed of at least one amphipathic lipid and at least one neutral lipid in one or more volatile water-immiscible solvents for the lipid component, an immiscible first aqueous component optionally and preferably containing a biologically active substance to be encapsulated, and optionally adding, to either or both the lipid component and the first aqueous component, an acid or other excipient for modulating the release rate of the encapsulated biologically active substances from the MVL. The mixture is emulsified, and then mixed with a second immiscible aqueous component to form a water-in-oil-in-water (w/o/w) second emulsion. The turbulence required for formation of the second emulsion is provided either mechanically (for example by rotor/stator, homogenizer, or other high-shear mixer), by ultrasonic energy, nozzle atomization, and the like, or by combinations thereof, to form solvent spherules suspended in the second aqueous component. The solvent spherules contain multiple aqueous droplets with the substance to be encapsulated dissolved in them (see e.g., Kim et al., *Biochem. Biophys. Acta* (1983) 728:339-48). For a comprehensive review of various methods of ULV and MLV preparation, see Szoka, et al., *Ann. Rev. Biophys. Bioeng.* (1980) 9:465-508.

The invention provides methods and processes for the production of liposome-based particles on a large scale, and methods for deriving the scale up parameters from smaller scale production processes. Aseptic methods are also provided in the present processes. Although sterilization of final filled container as a dosage form is often a preferred process in pharmaceutical manufacture for the assurance of minimal risk of microbial contamination in a lot, the MVL manufactured in the present processes are susceptible to unacceptable damage when subjected to some terminal sterilization techniques, such as autoclaving and gamma irradiation. In the absence of validated, non-damaging terminal sterilization, some embodiments of the invention utilize aseptic techniques, in which the product is prepared according to a carefully designed series of aseptic steps. These are designed to prevent the introduction of viable microorganisms into components, where sterile, or once an intermediate process has rendered the bulk product or its components free from viable microorganisms. Products defined as aseptically processed can consist of components that have been sterilized by aseptic means. For example, bulk products which are filterable liquids, can be sterilized by filtration. Final empty container components can be sterilized by heat; dry heat for glass vials and autoclaving for rubber seal components. The requirements for properly designed, validated and maintained filling and processing facilities are directed to: an air environment free from viable microorganisms, and designed to permit effective maintenance of air supply units; training of personnel who are adequately equipped and gowned. Available published standards for controlled work areas include: Federal Standard No. 209B, Clean Room and Work Station Requirements for a Controlled Environment, Apr. 24, 1973; NASA Standard for Clean Room and Work Stations for Microbially Controlled Environment, publication NHB5340.2, August 1967; and Contamination Control of Aerospace Facilities, U.S. Air Force, T.O. 00-25-203, Dec. 1, 1972, change 1, Oct. 1, 1974.

In aseptic processing, one of the most important laboratory controls is the establishment of an environmental monitoring program. Samples are collected from areas in which components and product are exposed to the environment, including mixing rooms and component preparation areas. Microbiological quality of aseptic processing areas is monitored to determine whether or not aseptic conditions are maintained during filling and closing activities. Routine sampling and testing of the room air, floors, walls, and equipment surfaces is carried out. This program establishes the effectiveness of cleaning and sanitizing equipment and product contact surfaces, and ensures that potential contaminants are held to an acceptable level. The disinfectants are checked to assure that their efficacy against normal microbial flora is maintained. Sampling schedules, including locations and frequency of sampling, are maintained. Passive air samplers such as settling plates (Petri dishes) are employed as well.

Aseptic assembly operations are validated by the use of a microbiological growth nutrient medium to simulate sterile product filling operations. These are known as "sterile media fills". The nutrient medium is manipulated and exposed to the operators, equipment, surfaces and environmental conditions to closely simulate the same exposure which the product itself will undergo. The sealed drug product containers filled with the media are then incubated to detect microbiological growth and the results are assessed to determine the probability that any given unit of drug product may become contaminated during actual filling and closing operations. Media filling, in conjunction with comprehensive environmental monitoring can be particularly valuable in validating the aseptic processing of sterile solutions, suspensions, and powders. Filling liquid media, as part of validating the processing of powders, may necessitate use of equipment and/or processing steps that would otherwise not be attendant to routine powder operations.

Clean-in-place (CIP) and sterilize-in-place (SIP) procedures are utilized. These procedures are generally known in the art. However, monitoring of the temperature at the steam traps is a part of the invention. According to this procedure, as steam is admitted into the vessels and fill lines to effect sterilization, the temperature at the outlet points is monitored until bacterial kill is assured. At this point, the seals are closed, and the system is sterilized for further use.

Sterility testing of product lots is carried out directly after the lot is manufactured as a final product quality control test. Testing is done in accordance with various procedures found in the U.S. Pharmacopeia (U.S.P.) and FDA regulations.

The individual process steps for large-scale production of such products are further detailed below.

First Emulsion

In the practice of the invention, the first emulsion is formed by high-shear mixing of two immiscible solutions. In general, one solution comprises liposome-forming lipids and/or oils dissolved in a water-immiscible solvent (which could be an organic solvent), and the other solution comprises a first aqueous formulation. A physiologically active compound is often added to at least one of the solutions, most typically at least the first aqueous phase. The first aqueous phase often also includes pH buffering agents, osmotic agents, release-modifying compounds, and the like. There can also be acids of various types included in the first aqueous phase, as detailed in copending U.S. patent application Ser. No. 08/792,566. The water-immiscible solvent phase can also contain biodegradable polymers or copolymers, as detailed in copending U.S. Patent Application No. 60/101,855 hereby incorporated by reference. The first emulsion is mixed by mechanical means, ultrasound, nozzle atomization, or the like, until the desired droplet size is reached. Static mixing (to be described in detail below) can also be employed at this stage, to make the first w/o emulsion.

In general, for making multivesicular liposomes, it is required that at least one amphipathic lipid and at least one neutral lipid be included in the lipid component. The amphipathic lipids can be zwitterionic, anionic, or cationic lipids. Examples of zwitterionic amphipathic lipids are phospholipids, such as phosphatidylcholines, phosphatidylethanolamines, sphingomyelins, lysophosphatidylcholines, lysophosphatidylethanolamines and similar substances. Examples of anionic amphipathic lipids are phosphatidylglycerols, phosphatidylserines, phosphatidylinositols, phosphatidic acids, cardiolipins and similar materials. Examples of cationic amphipathic lipids are acyl trimethylammonium propane, diacyl dimethylammonium propane, stearylamine, and ethyl phosphatidylcholine. Examples of neutral lipids are triglycerides, propylene glycol esters, ethylene glycol esters, and squalene. Examples of useful triglycerides are those including triolein and tripalmitolein, trimyristolein trilinolein, tributyrin, tricaprylin, tricaproin, and tricaprin. The fatty chains in the triglycerides useful in the present invention can be all the same, or not all the same (mixed chain triglycerides), including all different. Both saturated and unsaturated (including multiple unsaturated) fatty chains are useful in the present invention. The propylene glycol esters can be mixed diesters of caprylic and capric acids.

As used herein, the term "neutral lipid component" means the neutral lipid, or mixture of neutral lipids, used in manufacture of the multivesicular liposomes.

The neutral lipid component can comprise a single neutral lipid, or the neutral lipid component can comprise a mixture of a slow release neutral lipid and a fast release neutral lipid in a molar ratio range from about 1:1 to 1:100, e.g., from about 1:4 to 1:18, wherein the rate of release of the biologically active compound decreases in proportion with the increase in the ratio of the slow release neutral lipid to the fast release neutral lipid. For convenience, the molar ratio of the slow release neutral lipid to the fast release neutral lipid is referred to herein as "the slow:fast neutral lipid molar ratio."

The "slow release neutral lipid" can be selected from triglycerides having mono-unsaturated fatty acid ester moieties containing from about 14 to 18 carbons in the acyl chain and generally having a molecular weight from about 725 to 885, and those with saturated fatty acid ester moieties containing from about 10 to 12 carbons in the acyl chain and generally having a molecular weight from about 725 to 885; and mixtures thereof. One can use cholesterol esters such as cholesterol oleate and esters of propylene glycol. Exemplary slow release neutral lipids for use in the method of this invention include triolein, tripalmitolein, trimyristolein, trilaurin, and tricaprin, with triolein or tripalmitolein being most preferred.

The "fast release neutral lipid" can be selected from triglycerides having mono-unsaturated fatty acid ester moieties containing from about 6 to 8 carbons in the acyl chain and having a molecular weight from about 387 to 471, and mixtures thereof. However, the use of a neutral lipid component in MVL containing one or more neutral lipids with an acyl chain of six or less carbons (especially use of tricaproin as the sole neutral lipid) results in rapid release of the encapsulated compounds upon contact with the in vivo environment. Therefore neutral lipids with an acyl chain of six or less carbons should be used only in combination with one or more neutral lipids having a longer chain acyl moiety. Exemplary fast release neutral lipids include tricaprylin, and mixtures of tricaprylin and tricaproin, or mixed chain $C_6$ to $C_8$ triglycerides. Propylene glycol diesters with eight or ten carbon acyl moieties, cholesterol oleate, and cholesterol octanoate can also be used as neutral lipids.

The first emulsion can contain a number of useful substances, including flavoring or fragrant components, cosmetic products, waste materials, or pharmaceutical materials, including physiologically active materials. These substances can be introduced into either the aqueous or solvent phases. In certain preferred embodiments, the first emulsion can contain at least one physiologically active substance. This produces pharmaceutical compositions comprising MVL. Physiologically active substances are those natural, synthetic or genetically engineered chemical or biological compounds or entities that have utility for modulating physiological processes in order to afford diagnosis of, prophylaxis against, or treatment of an undesired condition in a living being. Physiologically active substances include drugs such as antianginas, antiarrhythmics, antiasthmatic agents, antibiotics, antidiabetics, antifungals, antihistamines, antihypertensives, antiparasitics, antineoplastics, antitumor drugs, antivirals, cardiac glycosides, hormones, immunomodulators, monoclonal antibodies, neurotransmitters, nucleic acids, proteins, radio contrast agents, radionuclides, sedatives, analgesics, steroids, tranquilizers, vaccines, vasopressors, anesthetics, peptides and the like. Prodrugs which form the indicated physiologically active substances upon local interaction with the intracellular medium, cells, or tissues can also be employed in the invention. Any pharmaceutically acceptable salt of a particular physiologically active substance which is capable of forming such a salt is also envisioned as being useful in the present invention, including halide salts, phosphate salts, acetate salts, and other salts.

Alternatively, the physiologically active substance could be hydrophobic and in this case it would be introduced into the water-immiscible solvent phase in the first emulsification stage. Amphipathic physiologically active substances can be introduced in either the aqueous or solvent phase, depending on their solubility in these phases.

Of particular interest are semisynthetic aminoglycoside antibiotics such as amikacin; antidiabetics; peptides such as insulin; antitumor drugs such as paclitaxel; antineoplastics including cytarabine, 5-fluorouracil and floxuridine; alkaloid opiate analgesics including morphine and hydromorphine; local anesthetics including bupivacaine; synthetic anti-inflammatory adrenocortical steroids including dexamethasone; antimetabolites including methotrexate; glycopeptide antibiotics including bleomycin; vincaleukoblastines and stathmokinetic oncolytic agents including vincristine and vinblastine; hormones, plasma proteins, cytokines, growth factors, DNA and RNA from a variety of organisms, and antisense oligonucleotides.

The physiologically active substances may be used singly or in combination with the limitation that the amount of the physiologically active substance in the pharmaceutical composition be sufficient to enable the diagnosis of, prophylaxis against, or treatment of an undesired condition in a living being. The pharmaceutical compositions can be administered to a living being by any desired route, for example, intramuscular, intra articular, epidural, intraperitoneal, subcutaneous, intravenous, intra lymphatic, oral, submucosal, transdermal, rectal, vaginal, intranasal, intraocular, and by implantation under different kinds of epithelia, including the bronchial epithelia, the gastrointestinal epithelia, the urogenital epithelia, and the various mucous membranes of the body. Generally, the dosage will vary with the age, condition, sex and extent of the undesired condition in the patient, and can be determined by one skilled in the art. The dosage range appropriate for human use includes a range of from 0.1 to 6,000 mg of the physiologically active substance per square meter of surface area. Alternate dosage range can be based on weight instead of surface area.

Referring to FIG. 1, which shows a schematic diagram of the significant components used in the inventive process, the continuous and dispersed phases are stored in two separate vessels, continuous phase vessel 1 and dispersed phase vessel 2. In the current processes, the continuous phase is an aqueous phase, and the dispersed phase is a water-immiscible volatile solvent phase. Any physiologically active substances to be encapsulated can be present in either vessel. Preferably, such substances are in the aqueous phase. These solutions are transferred simultaneously, sequentially or alternately into first emulsification vessel 3, passing through filters 4, which provide sterile filtration. The first emulsion (w/o) is prepared by emulsification using high shear mixer 5 or an equivalent device. Alternatively, static mixing (to be described in detail below) can also be employed to produce a first emulsion.

Sterile filtration of all fluids which enter the MVL production process is essential for an aseptic process, as envisioned in one embodiment of the present invention. Rating of pore sizes of filter membranes is by a nominal rating reflecting the capacity of the membrane to retain microorganisms of size represented by specified strains, not by determination of an average pore size and statement of distribution of sizes. Sterilizing filter membranes are those capable of retaining 100% of a culture of $10^7$ organisms of a strain of *Pseudomonas diminuta* (ATTC 19146) per square cm of membrane surface under a pressure of not less than 30 psi. Such filter membranes are nominally rated 0.22 μm or 0.2 μm, depending on the manufacturer. Bacterial filter membranes capable of retaining only larger microorganisms (including *Serratia marcescens* (ATTC 14756)) are labeled with a nominal rating of 0.45 μm. Filter membranes used in the present processes are of the 0.2 μm type, and are used in all lines feeding from liquid solution and gas storage tanks to vessels and transfer lines used to manufacture product.

During the mixing, the droplets of the discontinuous phase are deformed due to the shear exerted until the shear forces exceed the surface tension forces. At this point, the droplets are broken into smaller droplets. For a given aqueous and water-immiscible solvent system, the quality of the emulsion is controlled by the volume fraction of each phase, temperature, mixing speed and time. In addition, the choice of the vessel and shear device will affect the emulsion as well.

The characteristics of the w/o emulsion step can be determined by phase separation in a gravimetric field, droplet size distribution, emulsion viscosity, and conductivity of the continuous phase. A capillary viscometer can be used at high shear rates to determine the independent viscosity of an emulsion. Capillary viscometers are capillary tubes to which a pressure gauge and valve can be attached. Flow from the tube is measured and viscosity calculated according to the Hagen-Poisseuille equation:

$$Q=(\pi R^4 \Delta P)/8\mu L$$

where Q is the volumetric flow rate through the capillary tube, R is the radius of the capillary tube, ΔP is the pressure drop along the capillary tube, μ is the viscosity of the solution at the defined shear rate, and L is the length of the capillary tube.

Under given "lab-" or "bench-scale" process conditions, the experimentally determined viscosity will be the goal for larger scale processes. As described below, the viscosity is indicative of particle size in w/o emulsions. A set of "rules" are obeyed, whereby the same viscosity, and hence, the same particle size, can be achieved upon scale up. For example, by maintaining a constant shear blade diameter to vessel diameter ratio, the "lab-scale" (from about 0.1 to about 3 liters) viscosity can be roughly achieved at larger scales, up to 50 times the "lab-scale". Since the blade speed is defined by π times the blade diameter times the blade rpm, in a small scale process an emulsion is made with a determined viscosity. To achieve the same velocity at a larger scale, the vessel is chosen. Its diameter determines the blade diameter, and the blade speed is desired to be the same between the two scales. This allows a determination of the appropriate blade rpm. Comparison between the viscosity at the larger scale and smaller scale is made. To minimize discrepancy, a further method of achieving the "lab-scale" viscosity at a larger scale can be implemented. A correlation between energy input into an emulsion system and the independent viscosity of the emulsion exists. This correlation was found to be independent of scale for geometrically similar mixing systems.

The energy input into an emulsification is defined in Equation 1 as:

$$E/V = n^3 D^5 t/V \qquad (1)$$

where E is the theoretical energy input, n is the shear plate rpm, D is the shear plate diameter, t is the time, and V is the solution volume. The energy input per volume is scale independent. (Diaz, M., et al., "Mixing Power, External Convection, and Effectiveness in Bioreactors," *Biotechnology and Bioengineering*, Vol. 51, 1996, pp. 131-140). Application of this rpm to the larger scale results in the same viscosity at the different scales, and hence, the same particle size. This is a simple, rapid and reliable way to scale up emulsifications. Of course, the same procedure could be used to scale down a large scale emulsification, but practically, scale up is more often desirable.

Volume fractions of the dispersed phase to the continuous phase for the first emulsification can range from about 1.6 to about 0.33, and are preferably from about 6/4 to about 4/6. Impeller speeds for the first emulsification can vary from about 2000 rpm to about 16,000 rpm depending on the scale. For example, those emulsifications carried out at the bench scale can have impeller speeds of from about 8000 to about 16,000 rpm, and those carried out at the commercial scale range from about 2000 to about 5000 rpm. Mixing times for the first emulsification can vary from about 5 to about 100 minutes. Preferred mixing times range from about 10 to about 60 minutes.

Typically, the temperature of the reaction vessel is controlled by means of a water jacket. Mixing temperatures for the first emulsification can range from about 15° C. to about 40° C. Preferred mixing temperatures are from about 20° C. to about 32° C.

The droplet size in the first emulsion will vary depending on, energy input, the components used, the volume fraction of aqueous and organic solutions, and the desired stability and release profiles, but in general will be in the range of about 0.05 to about 3 μm, preferably from about 0.1 to about 1 μm. Droplet size can be determined directly (for example, microscopically), or indirectly, for example based on mixing time, or mixture viscosity. Different droplet sizes are obtained by varying the emulsification method (for example, by adjusting the impeller speed in the case of mechanical emulsification) and temperature.

Second Emulsion

The first emulsion is then mixed with a second aqueous solution, and emulsified to form a w/o/w emulsion comprising solvent spherules suspended in the second aqueous component.

The second aqueous solution can comprise pH buffering agents, osmotic agents, sugars, amino acids, electrolytes, preservatives, and other excipients known in the art of semi-solid dosage forms. Examples of such constituents include lysine, dextrose, and glucose.

The mixing and emulsification can be accomplished through mechanical means including high-shear type devices, rotor/stator and homogenizers, ultrasound, nozzle atomization, shear-type mixer, static mixer, impeller, porous pipe, or other means known to produce w/o/w emulsions.

Referring again to FIG. 1, the first emulsion is transferred from first emulsification vessel 3 to second emulsification vessel 7. This vessel can already contain the second aqueous phase, transferred from storage in second aqueous phase vessel 6, through in-line sterilization filter 8. Alternatively, the first emulsion and second aqueous phase can be introduced simultaneously, or the first emulsion can be introduced first. In one embodiment of the inventive process, a shear device is used to disperse the w/o emulsion in the second aqueous solution to form a w/o/w emulsion comprising solvent spherules. The solvent spherule size is dependent on the first emulsion quality, the second aqueous phase, and the volume fraction of w/o emulsion in the second aqueous solution. In addition, process parameters such as mixing speed, time, temperature and geometry of the mixing equipment will affect the w/o/w emulsion. The solvent spherules of the w/o/w emulsion are a labile process intermediate, and prompt progression to the solvent removal step is necessary.

The mixing times for second emulsifications carried out in shear-type mixers varies from about 1 minute to about 10 minutes. The temperature of the second emulsification vessel ranges from about 20° C. to about 50° C. Elevated temperatures can assist solvent removal in some embodiments of the invention.

Alternatively, the second emulsification is accomplished simultaneously by passing the first emulsion and the second aqueous solution through a static mixer. A particular suggested process schematic for this step is presented in FIG. 2.

Figure 2:
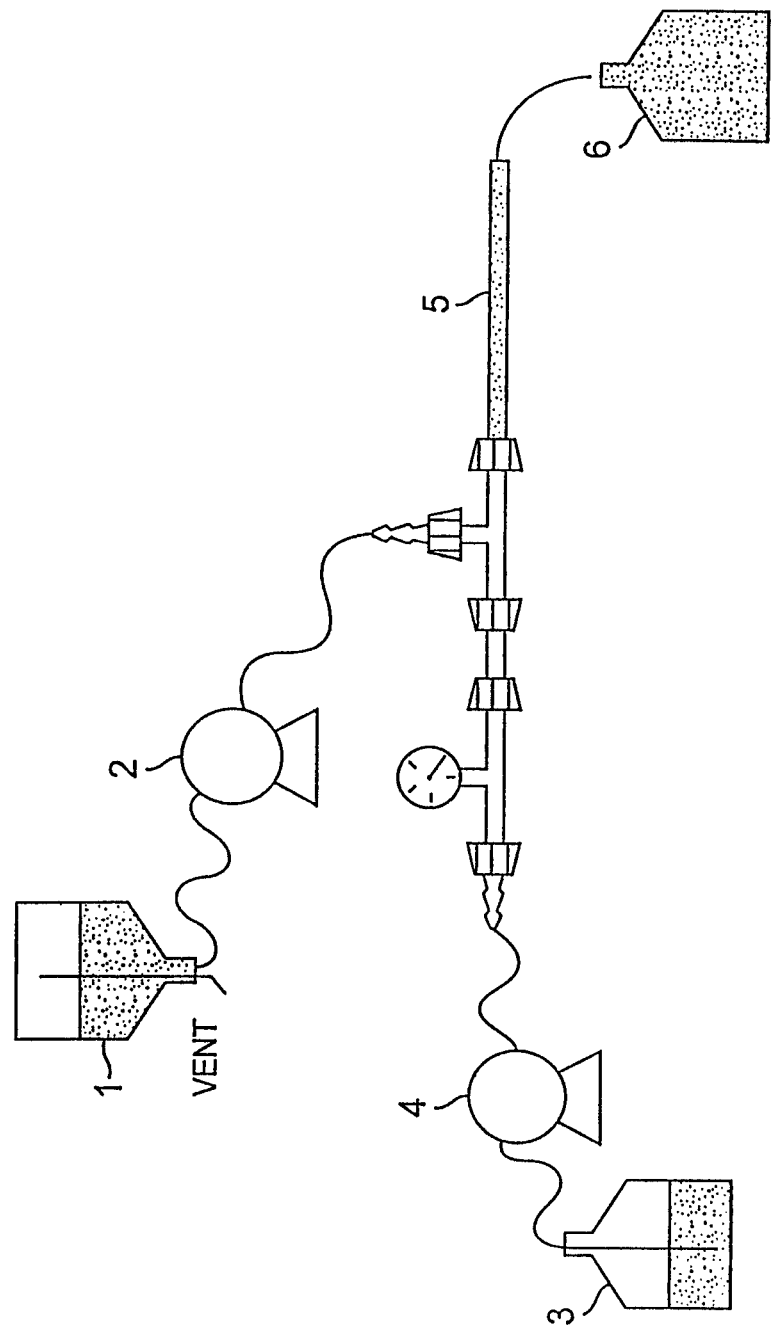
FIG. 2 is a schematic diagram of significant components used in a second particular embodiment of the inventive process.

Referring to FIG. 2, the first emulsion is contained in first emulsion vessel 1 and is fed through a feed line through first emulsion flow regulator 2 until it is mixed with the second aqueous phase, contained in second aqueous vessel 3. The flow of the second aqueous phase is monitored by a flow meter and regulated by second aqueous phase flow means 4 which could be a meter, control valve or pump. The mixed stream is then introduced into static mixer 5, which exits into second emulsion vessel 6.

Static mixers are available in a variety of sizes and designs: however, it is a matter of routine experimentation to select one capable of providing an emulsion having the desired particle size (and particle size distribution) at the desired throughput of material. Further, one can increase mixer diameter, or employ a number of static mixers in parallel to increase throughput, or in series to reduce particle size. Static mixers deployed in series or parallel can be used with other components, including a solvent removal means, between static mixers. Other components could be introduced into this stage of the process. For example, a thin film evaporator could alternatively be used as the initial solvent removal step. Static mixers include those made by Koch and Kenics, or static mixers of these general design types, as described further below.

Static mixers present a very attractive alternative to the high shear batch mixers for the preparation of emulsions. Some advantages of a static mixer compared to a stirred tank are the low capital cost, low complexity (including no moving parts), low maintenance cost and low space requirement. Furthermore, due to the structure of the static mixer, a more homogeneous mixing regime is possible since there are no "dead" regions. The utilization of a static mixer enhances the flexibility of existing process equipment since the batch size can be readily varied, and the mixer is readily adaptable to a continuous process. This concept is of special interest in a pilot plant where different processes utilize the same type of process equipment. Although static mixers have been used in the chemical and the food industry for the preparation of dispersions and emulsions, their use for the preparation of MVL has not been reported.

Static mixers are tubes with mixing elements inserted into the inner pipe. These inserts cause restrictions and impingement resulting in a high shear environment. When two streams, liquid and/or gaseous, are passed through the static mixer, various degrees of mixing are obtained. Depending on the miscibility and the combined velocities of the two streams, one can produce either a homogeneous solution, dispersion, or emulsion.

The various mixing elements in a static mixer create different types of mixing. Three different mixing actions can be observed in a static mixer: 1) two-by-two splits, 2) radial mixing, and 3) back mixing. A combination of two or three of these mixing actions occur simultaneously, the extent of which depends on the static mixer design.

The Kenics mixer contains mixing elements with a unique helical form that directs the flow of material radially toward the pipe walls and back to the element. By combining elements with alternating helical direction, the momentum of the radial mixing is reversed at each mixing element. The Koch mixer elements are corrugated sheets welded together to form open channels. Various elements can be inserted by positioning them 90° relative to each other.

For a given mixer design, the mixing action depends on the velocity through the static mixer and the shear rate applied to the fluid stream. For the preparation of an emulsion, droplets are broken into smaller droplets by extension and division. Linear velocities through static mixers according to the present process can range from about 100 cm/minute up to about 500 cm/minute. Preferred linear velocities are from 220 to about 400 cm/minute.

The emulsification or dispersion of two immiscible fluids using static mixers is dependent on various factors such as viscosity of the w/o emulsions, ratio of aqueous to water-immiscible solvent phase and mixer surface. The volume fraction of first emulsion to second aqueous phase can range from about 0.01 to about 0.5.

Solvent Removal

Once the second emulsion has been prepared, the volatile water-immiscible solvent is removed, resulting in MVL formation. Referring to again to FIG. 1, solvent removal can be performed in second emulsion vessel 7, in a vessel which serves as a sparging vessel but which is not necessarily equipped to perform the second emulsification, or directly in a static mixer, as described above. This is accomplished by bubbling an inert carrier gas through the solution using gas delivery means 9 such as a sparge ring or similar device. The gas delivery means generally has a number of holes through which the gas is introduced into the second emulsion. The number of holes can range from about 10 to about 10,000 or more. The holes have a specific diameter, which can range from about 0.001 to about 0.1 inches.

As an alternative, the carrier gas can be swept across the surface of thin layer of solution to remove the solvent, such as by flowing an inert gas counter to the flow of a thin film of second emulsion flowing over a packed column. The solvent removal rate is critical to obtain optimum product. It has been found that variations in solvent removal rate are important in optimizing product.

Figure 3A:
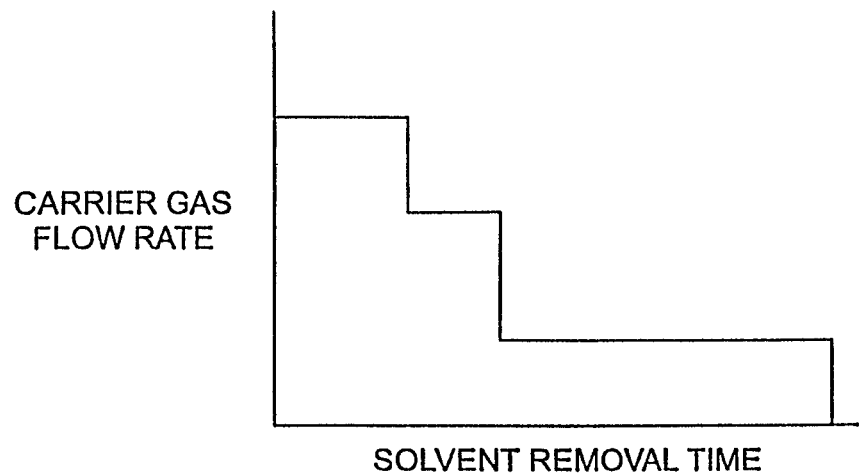
FIG. 3a is a carrier gas flow rate profile for a "high-low" step gradient.
Figure 3B:
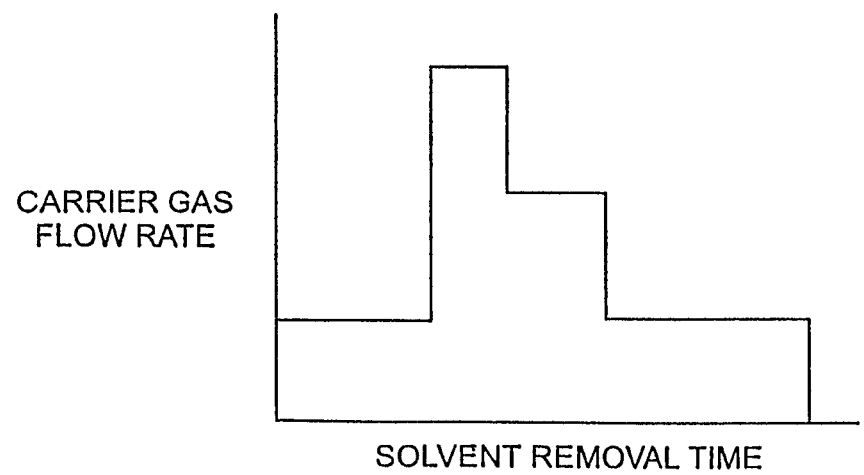
FIG. 3b is a carrier gas flow rate profile for a "low-high-low" step gradient.

There is a critical point during the solvent removal step, at which the optical appearance of the suspension changes significantly, for example, if the solvent is chloroform, it changes from a milk-like appearance to a more translucent appearance. Prior to this point, the multivesicular particles were found to be very susceptible to rupture and other damage. Therefore, the transition through this critical step needs to be as short as possible. If using a sparge setup, a quick removal of solvent at a high carrier gas flow rate followed by the slow removal of residual solvent at reduced flow rate (as in FIG. 3a) improved process yields. In order to reduce excessive foaming, an initially reduced rate until before the critical step, ramp up to high flow to transition through the critical step and then a reduced flow to remove residual solvents is an alternative profile (FIG. 3b). Foaming at later stages may be a greater consideration at lower production scales, such as the 1 L scale. Higher production scales, such as the 25 L scale, may not require the use of a reduced gas flow rate at later stages. Particular compositions may be more susceptible to foaming than others. For example, morphine-containing MVL may require somewhat lower initial flow rates, regardless of the scale. The flow rates, number of steps and duration of each step need to be experimentally determined for each product and scale.

Generally, the linear velocity of bubbles escaping from the gas delivery means at the 25 L scale should be less than or similar to that for the 1 L scale. Linear velocities for inert gas bubbles used for solvent removal can vary from about 20 inches/second to about 1000 inches/second, preferably from about 50 to about 800 inches per second.

In general, for the 25 L scale, a wide variety of solvent removal steps, inert gas flow rates and sequences can be utilized. For example, an initial solvent removal step using less than 500 lpm of inert gas flow (preferably less than about 400 lpm) for from about 3 to about 30 minutes (preferably from about 6 to about 20), followed by an inert gas flow of at least about 700 lpm (preferably at least about 1000 lpm) for from about 2 to about 10 minutes (preferably from about 3 to about 8 minutes), followed by an inert gas flow of from about 100 to about 400 lpm (preferably from about 150 to about 350 lpm) will produce acceptable results. Alternatively, the last flow step at reduced gas flow rate may not be required for acceptable product. In such cases, the inert gas flow of at least 700 lpm can be continued for from about 2 to about 90 minutes (preferably from about 5 to about 60 minutes). Flow rates for the 1 L scale are approximately 25 times lower, for example from 10 to 40 times lower. In any case, the gas flow must be sufficient to remove solvent at a rate which does not unnecessarily hamper the production of MVL.

Solvent removal (stripping) can be accomplished by sparging or blowing down with an inert gas, such as nitrogen or argon. For example, one can bubble nitrogen through the emulsion from sparge tubes or frits (if the scale is relatively small) supplied at the bottom of the container.

Primary Filtration

The resulting MVL product undergoes a primary filtration, for example by diafiltration or cross-flow filtration. The primary filtration step has several objectives: exchange the second aqueous solution by an isotonic solution, concentration of the multivesicular lipid based particles, removal of unencapsulated drug. Primary filtration, also known as diafiltration, is a method employed for the purification and separation of MVL from complex mixtures by virtue of the physical characteristics of MVL. For example, the most common physical characteristic used is size. This filtration involves cross-flow filtration, as opposed to dead end filtration. In cross-flow filtration, a suspension is circulated under pressure and in contact with a filter, so that permeate (the material which passes through the filter) leaves the system, and retentate (the material which does not pass through the filter) is left behind. The suspension then becomes concentrated in material that does not pass through the filter. In processes in which a first solution is to be exchanged for a second solution, the second solution is introduced on the retentate side of the filter, until the permeate gradually consists of the second solution. By this time, the first solution has been flushed from the suspension.

As illustrated in FIG. 1, during the primary filtration, the suspension of multivesicular particles is transferred into retentate vessel 10 and is recirculated through primary filtration filters 11 using retentate pump 12. Alternatively, pressure, from inert gas for example, can be used to carry out filtration. The primary filtration filters can be of various configurations and sizes, such as hollow fiber and plate and frame filters. Preferred filters are hollow fiber filters. These can be made of a variety of materials. Those made of polysulfone can be employed, such as those sold commercially by A/G Technology Corp. (Needham, Mass.). Other useful filters are fabricated from cellulose acetate, regenerated cellulose or polypropylene. Useful membranes include those rated at from 0.07 to 0.45 µm. Preferred membranes are from about 0.1 to 0.2 µm.

The pump can be of various types, such as peristaltic or rotary lobe positive displacement pumps. Permeate 13 is continuously removed until a preset weight is reached in the retentate vessel. The permeate can be controlled using a valve or pump or it may be allowed to flow freely. When a preset weight is reached in the retentate vessel, the exchange solution is added from storage tank 14 using pumping means 15 which can be a peristaltic pump or equivalent at the same rate as the permeate is removed. Alternately, the process can be driven by pressure, for example, inert gas pressure. The rate of adding the exchange solution can be controlled by matching the permeate flow rate or by maintaining a constant weight in the retentate vessel. After a number of volume exchanges or once the retentate reaches a target pH value, the addition of exchange solution is stopped. At this point, the retentate is concentrated to a final target weight.

Transmembrane pressures (sum of pressure at inlet of retentate and pressure at outlet of retentate, divided by two, minus the pressure at the permeate) can range from about 0.1 psi to about 7 psi. Retentate back pressures can range from zero to about 10 psi.

The primary strategy for optimizing a diafiltration step is to reduce fouling and gel polarization of the membrane. Basic process parameters such as wall shear rate, permeate flux and transmembrane pressure can be optimized in order to achieve this goal. However, the success is limited since the permeate flux can drop significantly during a diafiltration process.

To enhance the flux recovery and reduce the membrane gel polarization and fouling, permeate back pulsing can be used during the primary filtration process. Back pulsing is the intermittent, including periodic, reversal of the permeate flow in order to disturb the gel polarization layer and return particles into the retentate stream. Alternatively, back pulsing can utilize a separate countercurrent process stream to flush the primary filtration membrane. After a back pulse is completed, the permeate flux recovers to the initial value. This method results in a significant increase in average permeate flux and thus decrease the primary filtration process time for lipid based particles. The reduction of process time may increase the process yield for shear sensitive materials. In addition, the use of this method allows for semicontinuous production since multiple batches can be run before cleaning of the membrane is required. Thus, by the method of the invention, the capacity as well as the process time and yield for formulations of lipid-based particles, such as MVL, can be increased.

This following section describes the improvement of a primary filtration process with respect to time, capacity, and yield by the application of a back pulsing technique in the permeate for the primary filtration of multivesicular lipid based particles. The proposed setup includes the intermittent reversal of the permeate flow to remove the gel polarization layer on the primary filtration membrane. The solution used for back pulse can be any aqueous solution, such as a saline solution or permeate. The crucial process parameters to optimize are the transmembrane pressure (TMP), frequency and volume during the back pulse, and processing time.

Figure 4:
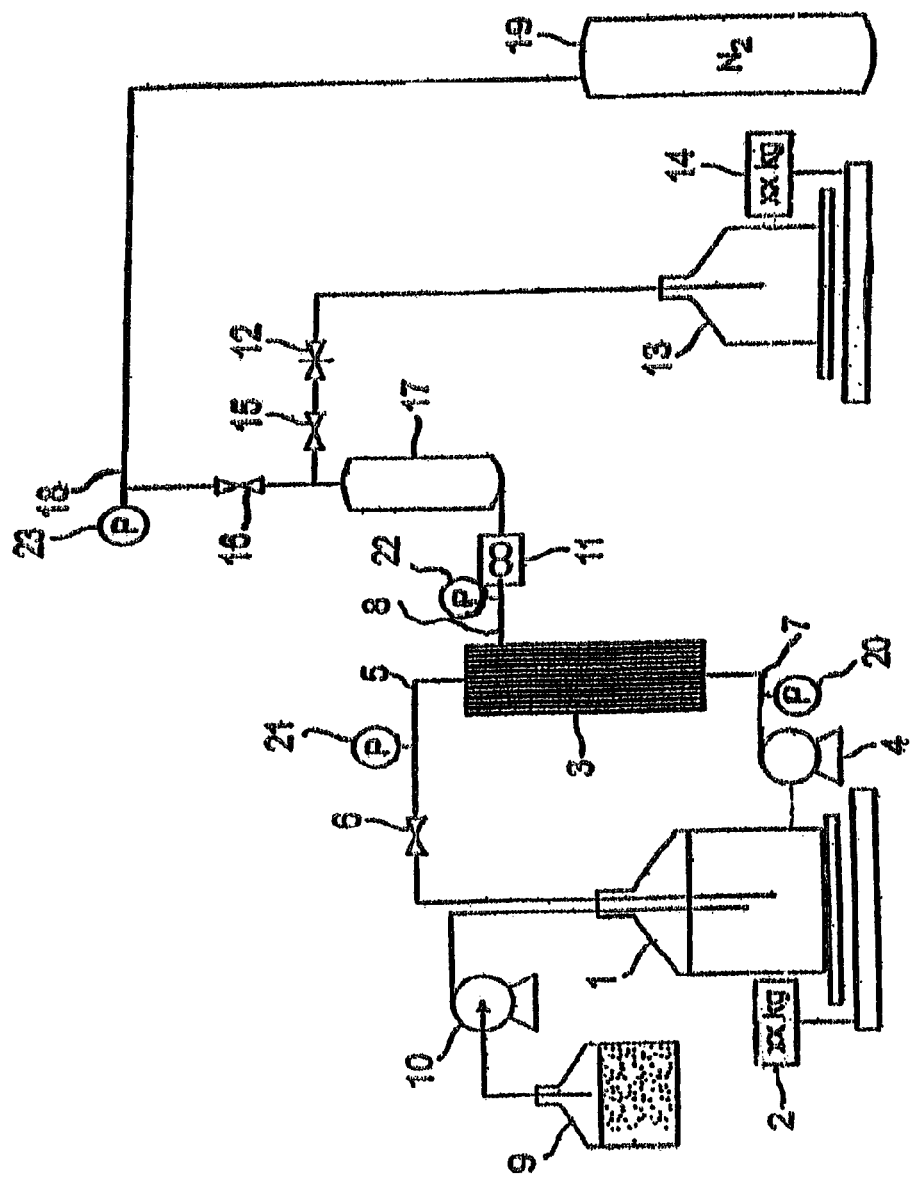
FIG. 4 is a schematic diagram of significant components of an experimental setup for diafiltration using permeate for back pulsing.

An example of a production set up for the back pulse using permeate is shown in FIG. 4. During the primary filtration process, the suspension in retentate vessel 1 located on means for maintaining constant weight 2 such as a scale or load cell, is recirculated through cross flow module(s) 3. These modules can be of any configuration if the manufacturer recommends the possibility of reverse pressurization of the membrane. Recirculation is achieved using retentate pump 4 of a peristaltic pump type or positive displacement pump type such as a rotary lobe pump. Back pressure is produced on the retentate return line 5 as desired by adjusting retentate valve 6. The transmembrane pressure during this operation can be monitored based on the pressure readings (P) 20, 21, 22 on retentate inlet 7, retentate return line 5 and permeate line 8 having pressure P. The buffer exchange solution is supplied from holding vessel 9 using pump 10 of the peristaltic or other type. During the normal operation, with the permeate in the forward direction, the permeate flow rate is monitored by flow meter 11 and controlled using control valve 12 such as a needle valve or other equivalent means for controlling flow. The permeate can be collected in waste container 13 monitoring the weight using weighing device 14 such as a scale or other equivalent apparatus. During the back pulse with the permeate in the reverse direction, the permeate flow is shut off with permeate valve 15. Inert gas valve 16 on the permeate side is opened pressurizing in-line permeate reservoir 17 at a pressure greater than the retentate pressure (P) 20, 21. This forces the permeate to flow in the reverse direction. The flow rate during the back pulse can be controlled by pressure P on inert gas line 18 supplied from inert gas reservoir 19. After a predetermined time period or until a predetermined volume of back pulse solution has been introduced, the normal filtration process is resumed.

Figure 5:
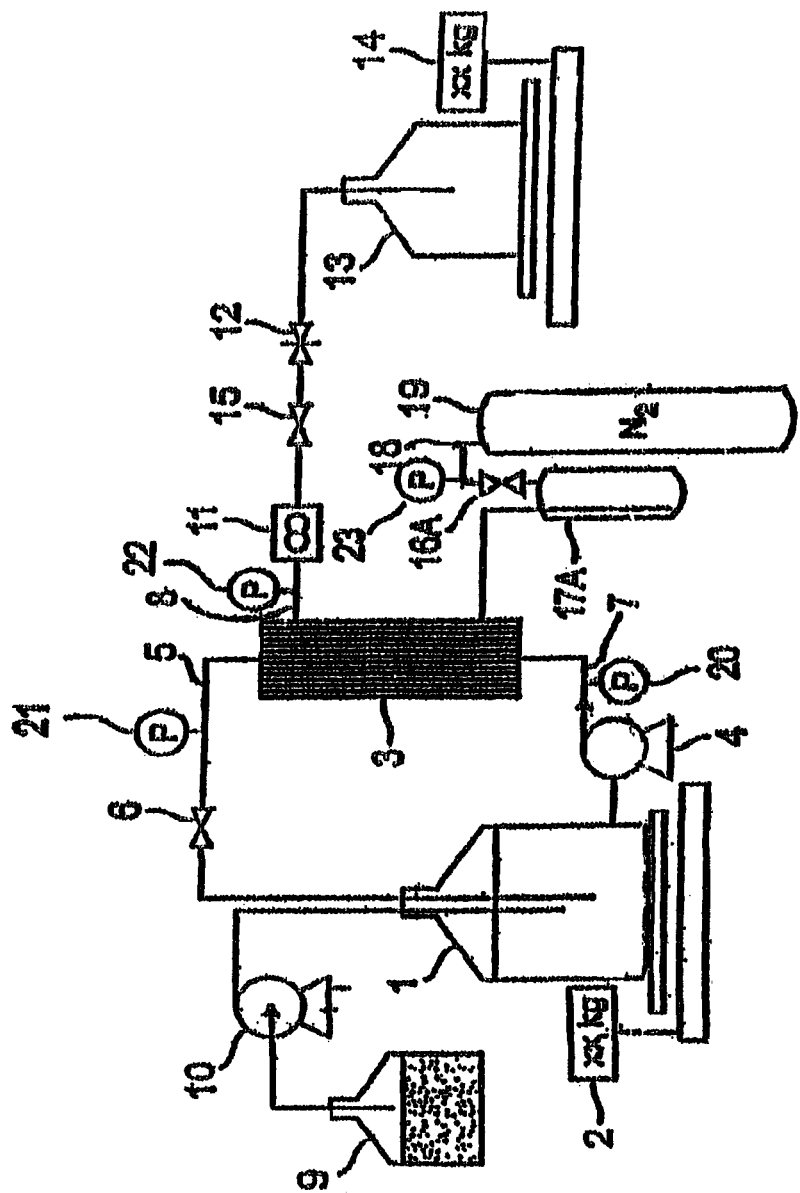
FIG. 5 is a schematic diagram of significant components of an experimental setup for diafiltration using saline or any other aqueous solution for back pulsing.

The setup for using saline or other aqueous solutions for the back pulse is similar to the setup used for the back pulse with permeate (FIG. 5). The setup for the actual primary filtration is the same as in FIG. 4 (items 1-15). However, the setup differs in the method for introducing the back pulse solution to the cross flow module. The back pulse solution is stored in vessel 17A that is under positive pressure (P) 23 from inert gas supply 19. During the back pulse using an aqueous solution other than permeate, permeate valve 15 is shut off, and back pulse valve 16A is opened. This allows the back pulse solution to flow in the reverse direction. After a predetermined time period or until a predetermined volume of back pulse solution has been introduced, the normal primary filtration process is resumed.

Back pulse volumes can range from about 0.05% system volume to about 2% system volume, but is preferably between about 0.1% and about 0.5% system volume. The interval between back pulses can range from about 10 seconds and about 10 minutes, but is preferably between about 1 minute and about 5 minutes. The "system volume" is defined as the volume of the material from the solvent removal step, and can be readily calculated from the back pulse time and the period between back pulses, given the flow rate.

Returning to FIG. 1, after the completion of the primary filtration step, the final product is transferred into storage vessel 16. The suspension of multivesicular particles may need to be adjusted to its final drug potency after completion of the primary filtration step. Procedures at this stage will differ depending on whether the material is too dilute or too concentrated.

If the material is too dilute, the concentration can be achieved in an additional microfiltration step using a smaller system than the primary filtration system. Alternatively, the supernatant can be decanted off after an extended settling period. For the decant, supernatant is removed from the post-primary filtration material after a settling time which is at least about 24 hours, but is preferably at least about 48 hours. This involves inserting a dip tube into the sterile bulk and aseptically pumping off supernatant until the pellet is substantially isolated. The material is then re-suspended for 15 minutes using a stir plate or equivalent device, and sampled by inserting a sterile pipette into the bulk. Due to sterility requirements, this operation is performed in a Class 100 environment. The adjusted bulk is then stored at 2-8° C. until the analytical results are obtained. In the event of low potency after the decant, the procedure can be repeated again, including the settling period. Alternatively, a secondary cross-flow filtration step (discussed in detail below) can be carried out.

If the material is too concentrated, the addition of isotonic solution can dilute it to the target concentration. Potencies of the physiologically active substances can vary over a wide range. For example, the potency of an MVL composition which contains protein may be on the order of μg/mL, whereas for other compounds, the potency range can be higher. For example, cytarabine-containing MVL potencies can range from about 5 to about 15 mg/mL, preferably from about 8 to about 12 mg/mL, most preferably from about 9 to about 11 mg/mL. For example, morphine-containing MVL potencies can range from about 5 to about 15 mg/mL, preferably from about 8 to about 12 mg/mL. Once the correct drug potency is reached, the material can be filled, using sterile filling procedures. Appropriate sterile filling procedures will become apparent to those skilled in the art.

Secondary Cross-Flow Filtration

Secondary cross-flow filtration is an alternative to decanting for adjustment of the bulk potency of physiologically active substance-containing MVL preparations. Additionally, the primary filtration step previously described may have too great a "hold ups", or dead volume to effectively reduce the volume to a desired value. Another major advantage of secondary cross-flow filtration is the elimination of the decant step, thereby reducing the risk of sterility breach significantly while saving operation time. Furthermore, the use of secondary cross flow filtration can improve product yields significantly. The secondary cross-flow filtration step can also be used to maximize efficiency by allowing the pooling of multiple product batches.

Figure 6:
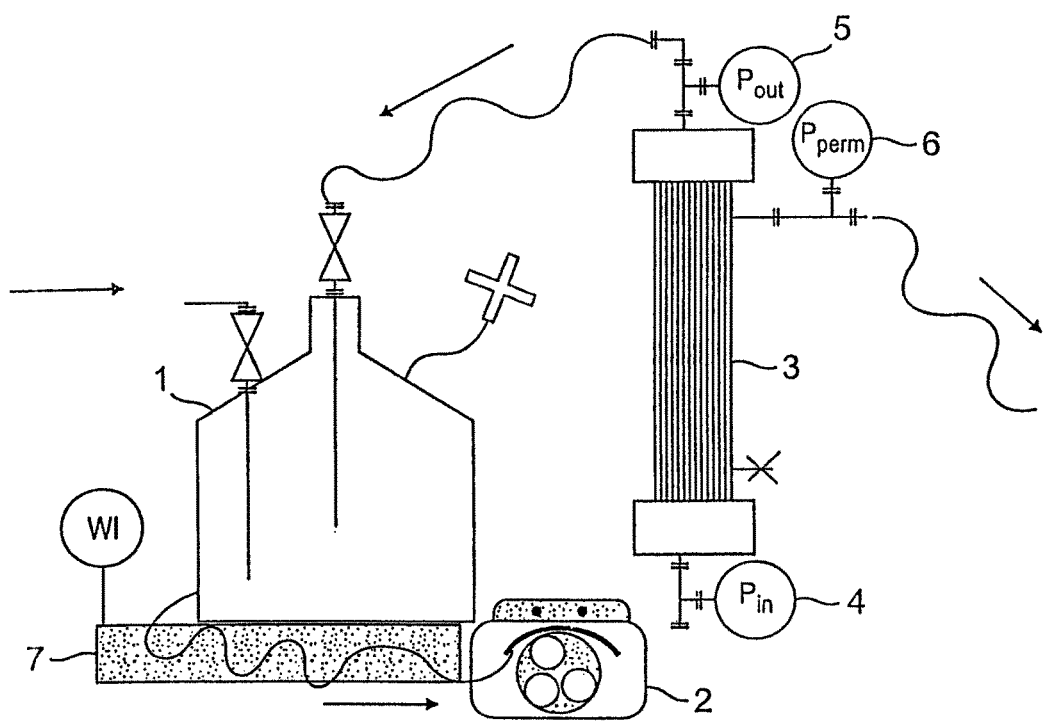
FIG. 6 is a schematic diagram of the significant components of an experimental setup for secondary cross-flow filtration.

A typical process set up is depicted in FIG. 6. Referring to FIG. 6, there is shown retentate vessel 1, which contains the product of the primary filtration step described above. This suspension of particles is pumped through a feed line by pump means 2, which can be a peristaltic pump, or other pump known in the art, into the inlet of secondary cross-flow filtration module 3. This can be a hollow fiber type module. Inlet pressure monitor 4 is present at the inlet of the module, and outlet pressure monitor 5 is present at the outlet of the module. The permeate is drawn off to be discarded or analyzed, but passes through permeate pressure monitor 6. The retentate outlet leads back to the retentate vessel, which is on weighing means 7 which allows monitoring of the progress of the secondary cross-flow filtration step. The retentate recycles through the cross-flow filtration module until a target concentration is reached. The target concentration is found to correlate linearly with the weight, so that a target weight can be calculated.

Secondary cross flow filtration is generally used in the inventive process to reduce volumes from the volume resultant from the primary filtration step to about 10% to 90% of this resultant volume.

Transmembrane pressures for secondary cross flow filtration can range from about 0.1 psi to about 7 psi. Retentate back pressures can range from zero to about 10 psi.

For pharmaceutically active-containing products prepared according to either a 1 L scale process or a 25 L scale process, final particle sizes range from about 13 to about 18 microns. The percent free drug ranges from about 0.3 to about 2.0%. The percent encapsulated active obtained from the entire process, calculated from total amount active introduced into the first aqueous solution, ranges from about 17 to about 50%. Such yields are dependent upon the particular product, and less dependent on the scale. Within a given product however, according to the inventive processes, the yields are highly reproducible.

The pharmaceutically active-containing MVL produced by the process of the invention can be used alone or in combination with other pharmaceutically active materials, with the limitation that the amount of the substance in the pharmaceutically active-containing MVL be sufficient to enable the diagnosis of, prophylaxis against, or the treatment of an undesired existing condition in a living being. Generally, the dosage will vary with the age, condition, sex, and extent of the undesired condition in the patient, and can be determined by one skilled in the art. The dosage range appropriate for human use includes a range of from 0.1 to 6,000 mg of the physiologically active substance per square meter of body surface area.

The pharmaceutically active-containing MVL of the invention can be administered parenterally by injection or by gradual infusion over time. The compositions can be administered intravenously, intraperitoneally, intramuscularly, subcutaneously, intracavity, or transdermally. Other methods of administration will be known to those skilled in the art. For some applications, such as subcutaneous administration, the dose required can be quite small, but for other applications, such as intraperitoneal administration, the required dose can be very large. While doses outside the foregoing dosage range can be given, this range encompasses the breadth of use for practically all physiologically active substances.

In connection with sterility, validation and environmental controls, a media fill validation program (FDA Guideline, June 1987, page 22 covering Aseptic Assembly Operations) was carried out regularly, using criteria which result in a high degree of confidence that the sterility assurance is well within or exceeds industry accepted standards.

All batches prepared have been subjected to the Bacterial Endotoxin Test (also known as the limulus amoebacyte lysate test—LAL), the Growth Promotion Test, and the Bacteriastasis and Fungistasis Tests, as detailed in the USP. In no case has any batch failed these tests.

The invention will be further described in the following examples, which do not limit the scope of the invention described in the claims.

EXAMPLES

The following examples are provided to further illustrate the invention by providing particular embodiments of the invention, and serve as a guide for those skilled in the art, and are not to be construed as limiting the invention in any way. All products are used according to manufacturer's instructions.

Particle sizing was performed on a Horiba LA910 particle sizer used in the standard mode, except where indicated otherwise. Samples (with volumes of between 50 and 400 μL, depending on product and sample concentration) for particle sizing were diluted in 10 mL of saline.

Lipocrit is a measure of the volumetric ratio of the solid pellet (after centrifugation) relative to the total volume of the suspension. Measurements were made by filling a hematocrit tube (Baxter B4416-1) with sample followed by centrifugation in an IEC Centra-4B centrifuge at 2200 rpm, or a Sorvall 6000D at 2000 rpm for 10 minutes.

Degree of encapsulation or encapsulation efficiency (% encapsulation) of any physiologically active substance in the suspension after solvent stripping or primary filtration was determined by UV spectroscopic methods, or by high performance liquid chromatography (HPLC). Samples were tested for both total and supernatant drug concentration. The percentage of free drug was calculated as % free=(1−Lipocrit)($C_{sup}$)/$C_{total}$), where $C_{sup}$ is the drug concentration in the supernatant, $C_{total}$ is the total drug concentration, and Lipocrit is the volumetric percentage of pellet. The degree of encapsulation is 100%−% free.

Viscosity measurements were measured using a capillary viscometer. The capillary viscometer is a silanized stainless steel tube (1.08 mm inside diameter, 50 cm in length, or 0.55 mm inside diameter, 50 cm in length; Alltech) attached to a pressure vessel and a digital pressure gauge and valve positioned at the entrance of the capillary tube. Flow from the tube was collected in a graduated cylinder. The viscometer was calibrated using Canon mineral oil standards with viscosities of 9.178 cP and 18.78 cP at 20° C. The first emulsion vessels were held at 20° C. during mixing unless temperature effects were being investigated. The temperature of the samples was recorded upon exit from the capillary tube. It did not vary more than ±5° with an average of 20.78° C. and standard deviation of 0.85° C. Second emulsion vessels were generally held at higher temperatures, for example 40° C.

For the determination of solvent removal, samples were taken each five minutes from a solvent spherule-containing composition undergoing solvent removal, and submitted for routine chromatographic analysis.

For all graphs presented, the lines fit through the data points represent the best fit to the experimental data.

Example 1

Viscosity as a Scale-Up Tool in First Emulsifications

The first emulsion process involved mixing two sterile filtered immiscible solutions at a specific impeller blade speed using a shear plate for a designated time. The first solution was a collection of polar and nonpolar lipids dissolved in a volatile water-immiscible solvent. The second contained an active drug in aqueous solution. Raw material quantities were scaled directly. To ensure that the first emulsion was consistent between scales, a dependent variable that was scale independent was chosen: viscosity. A relationship between viscosity and mixing time of the first emulsion has been established, as described in FIGS. 8a and 8b.

After the viscosity of the first emulsion was measured at the 1 L scale (12.8 cP), the agitator rpm at this scale was determined. The same blade speed of the shear plate at both the 1 L and 25 L scales where held constant. The blade speed is equal to the product of impeller diameter, π, and blade rpm. The ratio of impeller diameter to vessel diameter was held constant during scaling. Vessel diameters were scaled directly. Therefore, knowing the scaling factors, the scale up rpm was calculated. This approach resulted in a solution viscosity of 11.1 cP at this scale up rpm. Review of the data showed that the calculated rpm did not input sufficient shear into the emulsion to obtain the desired viscosity (12.8 cP). The next step was to use the energy input per unit volume to determine how much more power was necessary to increase the viscosity from 11.1 cP to 12.8 cP. This energy input per unit volume is defined in Equation 1 as:

$$E/V = n^3 D^5 t/V \qquad (1)$$

where E is the theoretical energy input, n is the shear plate rpm, D is the shear plate diameter, t is the time, and V is the solution volume. The energy input per volume is assumed to be scale independent. (Diaz, M., et al., "Mixing Power, External Convection, and Effectiveness in Bioreactors," *Biotechnology and Bioengineering*, Vol. 51, 1996, pp. 131-140). The additional energy per volume required to raise the viscosity in the scaled down system from 11.1 cP to 12.8 cP was calculated. This value was used to determine the new rpm for the scaled up system. Then viscosity was measured against time at the 25 L scale.

First emulsions were formed at four different scales ranging from 20 mL to 50 L. All mixers used high shear dispersion-type blades such as shear plates. Alternatively, a combination of a slotted cage and mixing cones could be used at higher scales (10 L to 25 L). The mixing speed and mixing time of the agitation were the parameters to be varied.

The w/o emulsions were formed by high shear mixing of an aqueous solution including 470 g morphine sulfate (Mallinckrodt Pharmaceuticals, Chesterfield Mo.), 85.8 g of 10% hydrochloric acid (Spectrum), and 22.6 kg water for injection. The water-immiscible solvent phase included the following surfactants: 32.0 g dipalmitoyl phosphatidylglycerol (DPPG, Avanti Polar Lipids, Alabaster, Ala.), 2123 g dioleoyl phosphatidylcholine DOPC (Avanti), and 114 g cholesterol (Spectrum). Also, 3.25 g triolein (Avanti) and 10.5 g tricaprylin (Avanti) were dissolved in the water-immiscible solvent phase (22.9 kg chloroform).

The first emulsion was carried out at 3600 rpm, for 960 seconds at 25° C. and 3 psig head space pressure in a first emulsion vessel equipped with a 4.5" mixing cage.

Figure 7A:
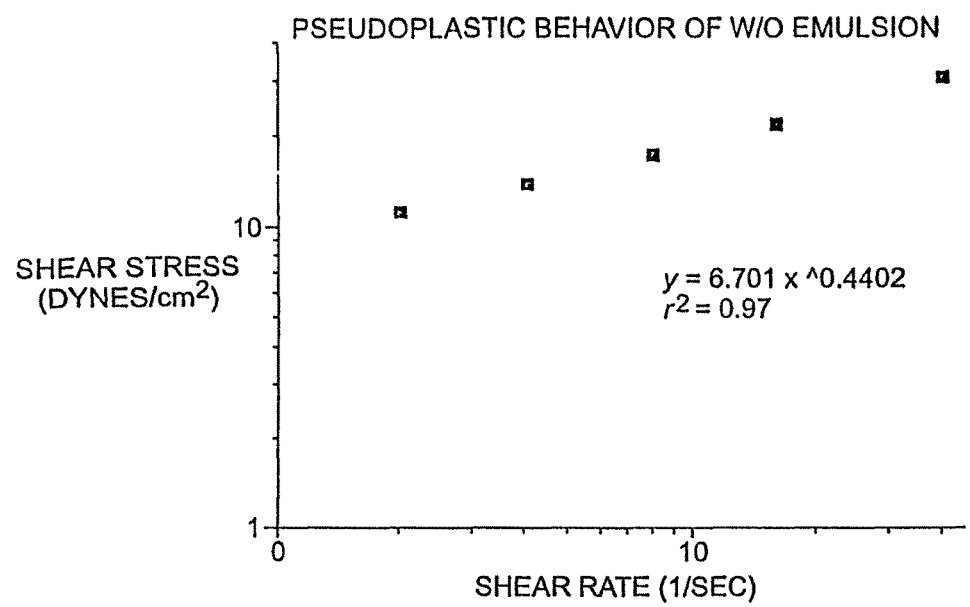
FIG. 7a is a graph of shear stress versus shear rate for a cytarabine w/o emulsion prepared as described in Example 1.

A rheological characterization of the w/o emulsion was obtained by measuring its relative viscosity over a large range of shear rates. The w/o emulsion was found to be pseudoplastic, resulting in a linear relationship between shear stress and shear rate when plotted on a log-log scale (FIG. 7a). The pseudoplastic nature of concentrated w/o emulsions is believed to be due the to the presence agglomerations at low shear rates which are broken-down and no longer present at the higher shear rates.

Figure 7B:
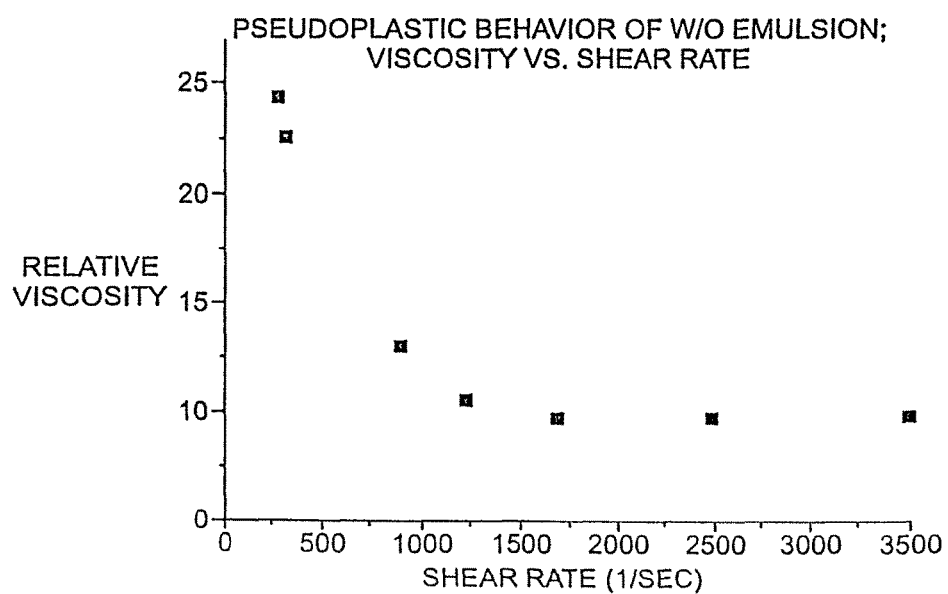
FIG. 7b is a graph of apparent viscosity versus shear rate for a cytarabine w/o emulsion prepared as described in Example 1.

FIG. 7b confirms the pseudoplastic nature of the emulsion by plotting relative viscosity (measured viscosity/continuous phase viscosity) versus shear rate. Viscosity decayed exponentially with respect to shear rate. In order to properly compare emulsion viscosities, experimental results were measured only within the equilibrium region of 2500 s$^{-1}$ and above.

Figure 8A:
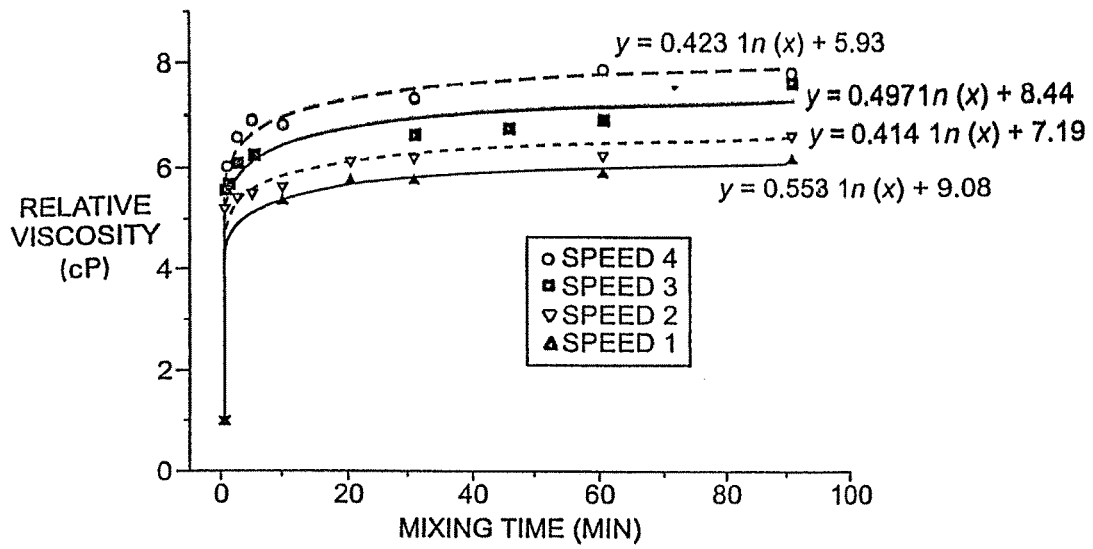
FIG. 8a is a graph of the effect of mixing time and speed on the relative viscosity of a cytarabine w/o emulsion prepared on the 100 mL scale as described in Example 1.
Figure 8B:
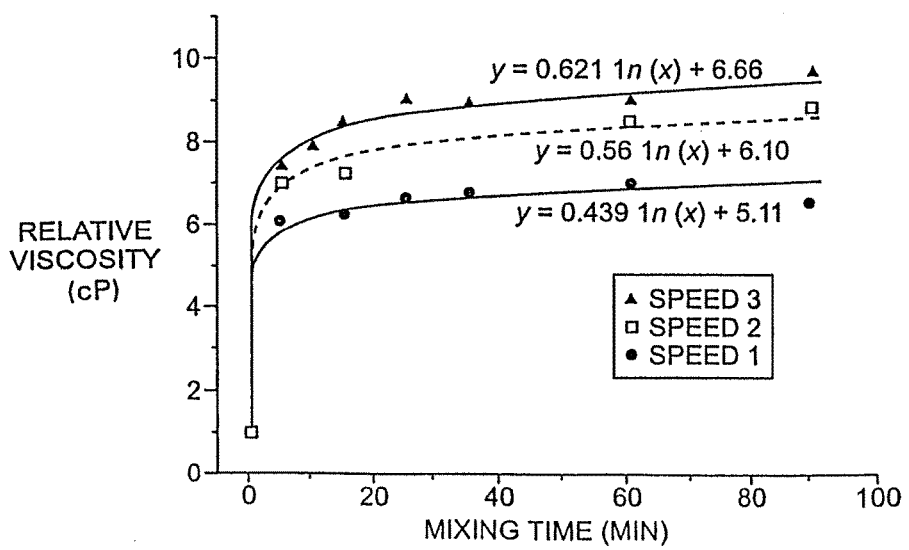
FIG. 8b is a graph of the effect of mixing time and speed on the relative viscosity of a cytarabine w/o emulsion prepared on the 400 mL scale as described in Example 1.

The w/o emulsions were prepared at several mixing speeds and times. The changes in mixing parameters resulted in emulsions varying in their independent viscosity (FIG. 8a). These results demonstrated a unique logarithmic increase in relative viscosity with increasing mixing time over a constant mixing speed. When the emulsions were scaled by a factor of four the same logarithmic relationship between mixing time and viscosity was observed (FIG. 8b).

Figure 9:
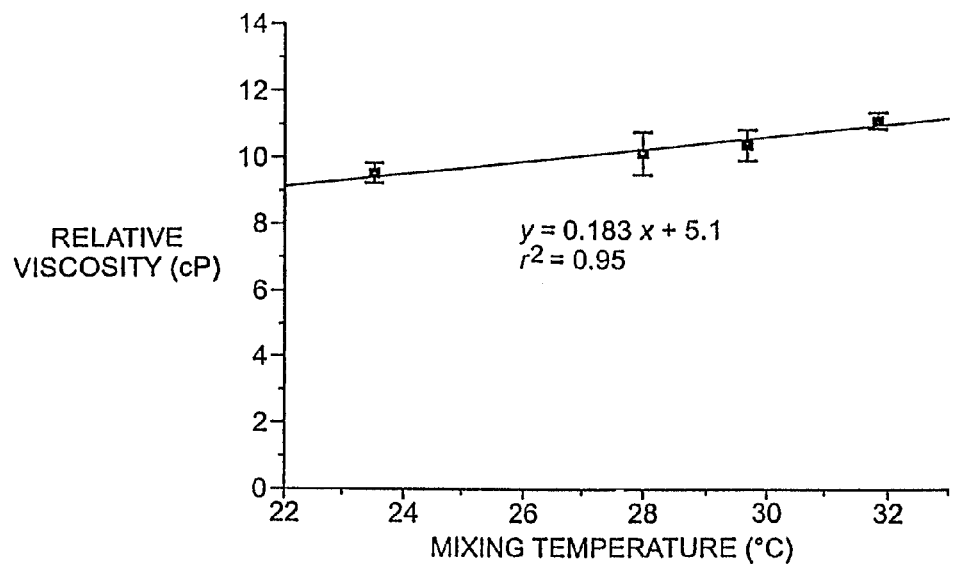
FIG. 9 is a graph showing the effect of mixing temperature on the emulsion viscosity of a cytarabine w/o emulsion prepared at the 400 mL scale as described in Example 1.

Several w/o emulsions were prepared at temperatures ranging from 22° C.-32° C. The effect of formation temperature on emulsion viscosity was characterized in FIG. 9, showing that emulsion formation temperature had a direct linear effect on emulsion viscosity. At higher temperatures the lipid membrane became more malleable and droplets were easily broken-down. In this manner, emulsions made at higher temperatures had a smaller mean droplet in size and therefore a higher apparent viscosity.

Additional viscosity measurements were made with the capillary viscometer using a capillary tubing of smaller diameter in order to determine if wall effects were present. The fact that both measurements overlapped confirmed that the wall effects in the capillary viscometer were insignificant for our purposes. If wall effects had been present, we would have expected to see greater wall effects, lower viscosity, with the smaller diameter tubing.

Figure 10:
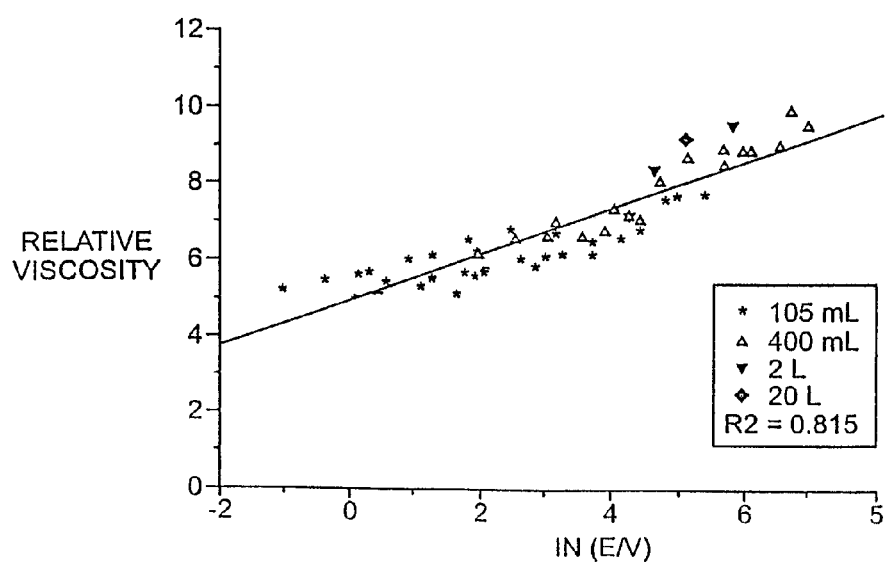
FIG. 10 is a graph showing the linear relationship between relative viscosity and the natural log of energy input per unit volume for a cytarabine w/o emulsion prepared at scales ranging from 0.1 L to 20 L.

In order to better utilize the relationship between viscosity and energy input, the graph was linearized by plotting energy on a logarithmic scale (FIG. 10). Additionally, data at two of the larger scales was added. A linear relationship between w/o emulsion viscosity and the energy input to the emulsion was established over a 200-fold scale increase. In this manner a desired emulsion viscosity can be chosen and the corresponding necessary energy input can be found in FIG. 10. At a given scale the mixing speed and time can then be varied to achieve the needed energy input.

Example 2

Particle Size as a Scale-Up Tool in Second Emulsifications

A water-oil-water emulsion was formed by blending the first emulsion with a much larger volume of a second aqueous solution. Final particle diameter and size distribution were a function of impeller configuration, rpm and mixing time. Particle size and distribution were measured using a particle size analyzer (Horiba, model 910). Shear plate diameter and rpm were scaled from the 1 L system following the procedure used in the first emulsion system.

The second aqueous solution consisted of: 21.88 kg dextrose, 503 g lysine, and 382 kg of water for injection. Initial scale-up calculations for the second emulsion of the morphine-containing preparation of Example 1 at the 25 L scale indicated a 9.0 inch shear plate at 500 rpm should be used. However, under these mixing conditions, the solution was not adequately mixed. The low rpm did not sufficiently blend the denser first emulsion with the second aqueous solution. Furthermore, high density regions within the reactor made the solvent stripping process ineffective. Particles generated under these conditions were 10 to 12 μm. The particle size specification for this product is 13 to 18 μm.

Agitation speed had to be increased to blend in the first emulsion. Through observation, 1000 rpm proved sufficient. At the higher rpm, particle size would become even smaller. The energy input per volume was maintained by reducing the impeller diameter from 9.0 inches to 4.5 inches. The shear plate was replaced with a 4.5" slotted cage. The mixing time was 300 seconds at 40° C. at 1000 rpm.

This process generated 14 to 16 micron particles. The solvent stripping process was also dramatically improved, as the improved mixing fully dispersed the dense layer of chloroform that can remain at the bottom of the shearing tank, allowing it to be more efficiently removed by the inert gas stream.

The particle size standard deviation was reduced from 6.2 to 4.5 μm when the 9.0 inch shear plate was replaced with the 4.5 inch slotted cage. There are two likely reasons for this significant reduction in particle size standard deviation. First, at higher rpm, more solution was exposed to the shearing edge. Increased exposure reduced overall size variability. Second, the slotted cage imparted uniform shear to all particles that passed through it. The shear exposure from a shear plate was not uniform.

Example 3

Solvent Removal

The w/o/w emulsion generated in the second emulsification step of Example 2 still contained solvent at this point. Solvent was stripped from the emulsion through gas sparging. Controlling the rate of solvent removal was critical. During stripping, regular samples were taken to measure solvent concentration and to monitor drug encapsulation. If the concentration of free drug began to increase during stripping, particle damage was occurring. Initial gas flow rates were increased 25-fold to match the volume increase. Processing time for the solvent stripping was initially held constant between scales. Once the solvent was removed, the particles became rigid and more stable.

Figure 11:
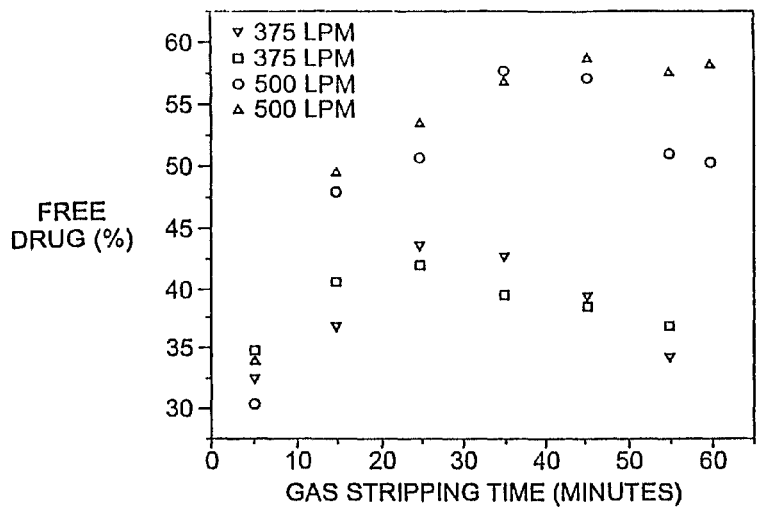
FIG. 11 is a graph showing the effect of gas stripping time at 375 and 500 liters per minute on the percentage of free morphine.

The initial sparging profile of the 25 L morphine-containing solvent spherule system, based on the 1 L process, used three different flow rates. The first stage set the flow at 375 liters per minute (lpm) for 17 minutes. Then the solution was sparged at 1000 lpm for 5 minutes, followed by 250 lpm for 28 minutes. The reason for reducing the flow rate of the first and last stages at the 1 L scale was to reduce foaming, which can be a concern during the first 10-20 minutes for morphine-containing preparations. In the 25 L process, foaming was not found to be a significant problem at the later stages, due to the use of a vessel of relatively tall and narrow shape. If this vessel was not used, and the initial sparge rate is higher than 500 lpm, the foam trap fills to capacity. Also, at 500 lpm in the shorter, squatter vessel, it was noted that the percentage of "free drug" (unencapsulated physiologically active substance) significantly increased, indicating particle disruption. This is presented in FIG. 11.

At 375 lpm, the "percent free drug" was similar to that seen at the 1 L scale. In all 25 L experiments, sparging at 1000 lpm after 17 minutes did not effect encapsulation efficiency, and additional foaming was negligible. Four identical second emulsions were stripped of solvent under identical conditions in order to prove that the solvent was consistently removed below the specified concentration of 100 ppm. The data showed that 17 minutes of sparging at 375 lpm followed by 25 minutes of sparging at 1000 lpm was sufficient to reduce the solvent concentration below 100 ppm. The solvent concentration was routinely brought to less than 1 ppm within 60 minutes of solvent removal. Four identical batches proved that the solvent removal process was reproducible.

Figure 12:
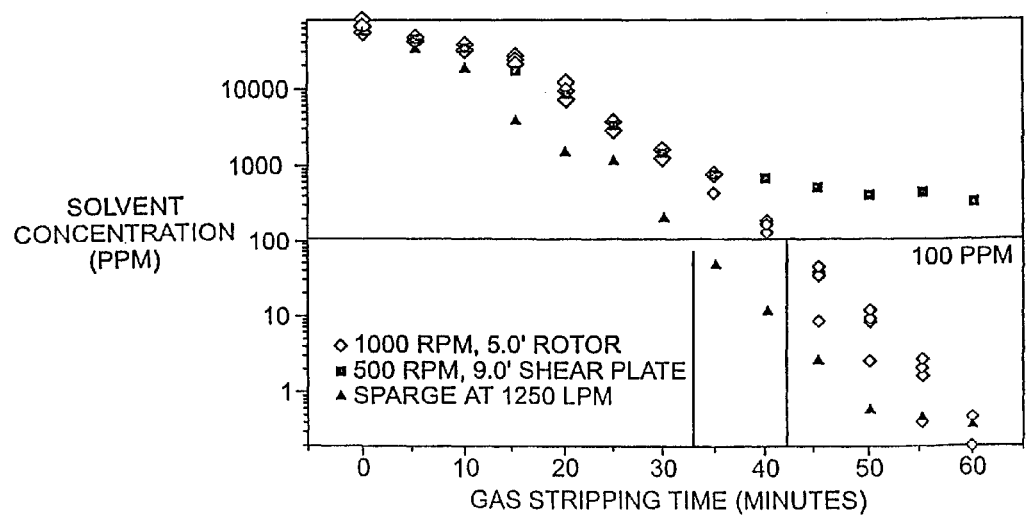
FIG. 12 is a graph showing the effect of gas stripping time on the solvent concentration for two different high-shear emulsion conditions at different gas flow rates: 375 LPM for 17 mins, 1000 LPM for the remainder of time.

The minimum possible stripping time was determined by sparging with the maximum available flow rate of 1250 Lpm. This experiment shows that, at best, only 9 minutes could be shaved off the current processing time. This is shown in FIG. 12. Under these conditions, the foam trap was completely filled and the percent free was over 50%. For these reasons, the current processing time of 42 minutes was deemed acceptable.

Example 4

Scale-Up of Buffer Exchange and Concentration

After solvent stripping of the particles from Example 4, the particles were suspended in a solution that is generally not suitable for injection. Thus, the morphine-containing suspension was transferred to a cross-flow filtration skid where it was concentrated and the second aqueous solution was exchanged for saline or other physiological solution. Parameters studied during cross-flow are: processing time, permeate flow rate, step yield, and final product stability. In scaling, linear velocity through the tangential flow filters was held constant. Filter area was increased to provide the desired permeate flow rate. In design, hold up of the cross-flow system was minimized.

This product was chemically stable over two years in cold storage. An accelerated stability protocol was established to shorten the time required to collect data. Currently, the release specifications for morphine required that the percent of free drug in solution could not exceed ten percent of total encapsulated drug prior to 21 days at 37° C. Final product was vialed and stored at 37° C. Samples were regularly taken over time and analyzed for percent free drug.

Initial engineering design of the cross-flow filtration system reduced the need for process development. From the first runs, concentration and buffer exchange performed as expected. Permeate flow rates were constant throughout the process at 5.0 LPM. Processing time was relatively consistent with the 1 L process at 2.5 hours. The step yield for the cross-flow filtration was 85 percent. Overall encapsulation efficiency was 41 percent which was consistent with the yield at the 1 L production scale.

The material produced at this scale was very stable. Stability data from showed that percent free drug did not exceed the maximum ten percent until day 38 at 37° C. Current stability criteria dictate that acceptable product exceed 21 days at this temperature. Similar acceptable results were obtained from cytarabine preparations.

Example 5

Multiple Batch Processing

In routine pharmaceutical production, clean-in-place (CIP) and sterilize-in-place (SIP) processes consume the major portion of the processing time. Thus, in conventional processes, only about 30% of the time is dedicated to direct manufacturing steps and the rest is cleaning and sterilizing for the next batch.

The present invention provides multiple batch processing. Multiple batch processing involves the production of identical batches, and subsequent or sequential pooling of batches for further downstream processing, thus making more efficient use of "down time", during CIP and SIP cycling.

Figure 13:
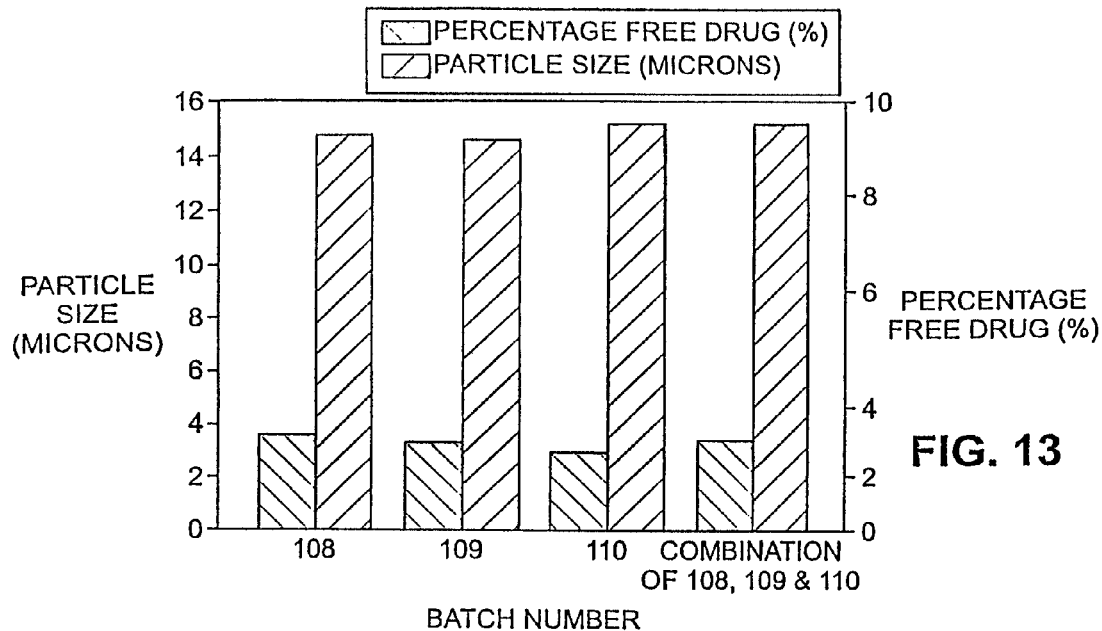
FIG. 13 is a bar graph of a comparison of three lots of morphine-containing preparations and a pooled preparation showing the percentage free drug and particle size.

In a 1 L scale, morphine-containing preparation, three lots of product were produced and pooled after after the solvent removal step and SIP, but prior to cleaning. Each lot and the pooled composition were analyzed for percent free morphine, and particle size. The data is presented in FIG. 13.

Excellent consistency between consecutive lots was obtained, as expected. The most significant concern arose in connection with the cross-flow filtration step, which utilizes filters which could have become fouled with extended use. Back pulsing was applied to this system for part of the second, and most of the third lots. Back pulsing did not affect product quality. The 25 L system was specifically designed to operate at 75 L using this multiple batch processing.

Example 6

Static Mixing

The following materials were prepared for testing with static mixers. For a 25 L scale, morphine-containing preparation static mixer process, the chemical components and quantities were as listed in Examples 1 and 2.

A cytarabine preparation was made up with a first aqueous phase of 30 g/L cytarabine and 51.31 g/L HCl (10% w/v), a volatile water-immiscible solvent phase of 2.06 mg/mL DPPG, 2.15 mg/mL triolein, 7.66 mg/mL cholesterol, 10.34 mg/mL DOPC, and 0.76 mL/mL water for injection (WFI) in chloroform, and a second aqueous phase of 70.6 g/L dextrose (50%), and 6.29 g/L L-lysine. Cytarabine was prepared at the 10 L scale.

A morphine preparation was made up with a first aqueous phase of 21.32 g/L morphine sulfate, and 3.84 g/L HCl (10% w/v), a water-immiscible solvent phase of 2.081 mg/mL DPPG, 0.211 mg/mL triolein, 7.72 mg/mL cholesterol, 9.58 mg/mL DOPC, 0.683 mg/mL tricaprylin, and 0.764 mg/mL WFI in chloroform, and a second aqueous phase of 152 g/L dextrose (50%), and 1.59 g/L L-lysine. Morphine preparations were made at 1, 10 and 25 L scales.

An insulin-like growth factor (IgF-1) preparation was made up with a first aqueous phase of 14.5 g/L IgF-1 in 5% sucrose/20 mM citrate, a water-immiscible solvent phase of 2.08 mg/mL DPPG, 1.79 mg/mL triolein, 7.68 mg/mL DEPC, and 1.492 mg/mL WFI in chloroform, and a second aqueous phase of 1.49% glycine, 0.041 N $NH_4OH$, and 329.2 g/L L-lysine.

Amikacin preparations were made up with a first aqueous phase of either 80 g/L amikacin free base, in 168 g/L sulfuric acid (pH 8), or 60 g/L amikacin free base in 50.9 g/L sulfuric acid (pH 9), a water-immiscible solvent phase of 2.07 mg/mL DPPG, 2.16 mg/mL triolein, 7.69 mg/mL cholesterol, 10.4 mg/mL DOPC, and 0.78 mL/L WFI in chloroform, and a second aqueous phase of 95.84 g/L sucrose, and 6.56 g/L L-lysine.

First emulsions of each preparation were prepared using a high shear stirred tank (100 mL, 400 mL, 2000 mL and 40 L), until the desired particle size was reached. Particle size was determined using a Horiba LA910 particle sizer, using samples of 50 µL or 400 µL diluted in 10 mL of saline.

The volume ratio of the first emulsion feed stream to the second aqueous phase feed stream was unique for each process, but was in general varied from 0.075 to 0.35. The feed streams were supplied to a static mixer using either a rotary lobe pump or a nitrogen-pressurized vessel as the driving force. The following Kenics™ Static Mixers were used: 3/16" OD, with 27, 16, or 9 elements; 1/4" OD with 21 elements; 1/2" OD with 21 elements; and 1.5" OD with 24 elements. The following Koch static mixer was used: SMV-DY mixer, 1/4" with 5 elements. The following pumps were employed: Watson Marlow pump model #604S; Cole Parmer pumps model #7523-20; and G+H rotary lobe pump, model #GHPD322.

The flow rate of the first emulsion into a receiving vessel immediately before the static mixer was monitored by an in-line flow meter (Flow meter, EG&G, model #FT6-871W-LEGA1), and was controlled by a valve on the pressure vessel outlet. Flow rates are scale dependent and therefore not useful for scaling up. More useful are the linear velocities, which are determined by dividing the flow by the cross-sectional area of the particular static mixer used.

Figure 15:
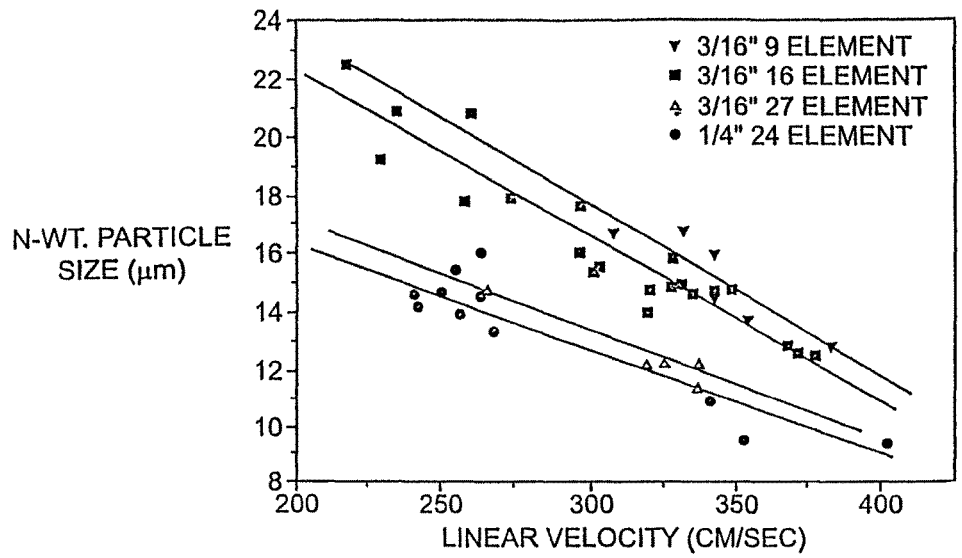
FIG. 15 is a graph showing the effect of linear velocity through static mixers of various sizes and configurations on the particle size of cytarabine-containing preparations prepared at the 0.2 L scale.

The first emulsion was supplied at 25° C., while the second aqueous solution was supplied at 35° C. Flow rates are dependent on the size of the static mixer, but the linear velocity was held constant for different static mixer sizes. Representative linear velocities are shown in FIG. 15. Therefore, if a 1/2" O.D. Kenics mixer (0.11 $inch^2$ surface area) was run at 4.9 lpm, a 1.5" O.D. Kenics mixer (1.48 $inch^2$ surface area) would be run at 66 lpm. The receiving vessel maintained the resulting second emulsion at 35° C. Solvent removal was then carried out. Chloroform was removed by blowing down with $N_2$ (100 mL scale) or sparging with $N_2$ (larger scales). Blowing down was effected by placing 50 mL samples into 1 L Erlenmeyer flasks in a rotating water bath set at 37° C. The flasks were sealed except for one $N_2$ supply line and a vent line for $N_2$ and $CHCl_3$. Nitrogen was applied at a rate of 55-75 SCFH for 15 minutes.

The resulting suspension was concentrated by cross-flow filtration, using 0.2 µm polysulfone hollow fiber membranes (A/G Technology, CFP-2-E-5A, 0.2 µm pore size). Sparged material was processed in three steps: initial concentration, primary filtration, and final concentration. Initial concentration concentrated the material to half the original volume. Diafiltration was used to exchange the second aqueous solution with an acidified saline solution. The final concentration step was used to bring the product to its specification volume.

Product analyses of total and free drug were carried out as follows. For determination of total cytarabine, 0.5 mL of second emulsion sample was diluted and the particles were lysed with 0.5 mL of isopropyl alcohol (IPA). These samples were then vortexed for several seconds. Next, 100 mL of vortexed sample were diluted to 10 mL with 0.1 N HCl. The absorbance of the samples were read using UV spectrophotometer (Cecil) at 280 nm. For determination of supernatant (free) cytarabine, 1 mL of second emulsion sample was pipetted into Eppendorf vials and centrifuged in an Eppendorf centrifuge for 2.5 minutes at a setting of 8.5. An aliquot of 100 µL of this supernatant was then diluted to 10 mL with 0.1 N HCl. The absorbance of the sample was then read using a UV spectrophotometer at 280 nm.

For determination of total morphine, 250 µL of second emulsion sample was diluted and the particles were lysed with 750 µL of IPA. These samples were then vortexed for 15 seconds. Next, the vortexed sample was diluted to 1:10 with 2% sodium hydroxide/0.8% normal saline solution and vortexed. The absorbance of the samples were read using UV spectrophotometer (Cecil) at 280 and 340 nm. For determination of supernatant (free) morphine, 1.0 mL of second emulsion sample was centrifuged for 2.5 minutes at the setting 8.3 using an Eppendorf centrifuge. An aliquot of 100 µL of this supernatant was then diluted in 10 mL of sodium hydroxide/normal saline and vortexed for 15 seconds. The absorbance of the sample was then read using a UV spectrophotometer at 280 and 340 nm.

For determination of total IgF-1, 100 µL of second emulsion sample was diluted in 900 µL of 87.5% IPA/12.5% 2N HCl and vortexed. After 45 minutes on ice, 200 µL of 1M Tris solution, pH 9 was added and vortexed again. The sample was microfuged at 14,000 rpm for 2 minutes, and 200 µL of sample was added to 800 µL of 10% acetonitrile (ACN)/0.2% trifluoroacetic acid (TFA) in an HPLC vial and run on the HPLC. The HPLC was a Waters Symmetry $C_{18}$ (P/N WAT054205) with guard column, P/N WAT054225. The run time was 17 minutes with a 9 minute post time (oven temperature 45° C.). The initial flow rate was 0.8 mL/min with a 100 µL injection volume with a 167 µL draw speed. A DAD detector was used, sampling every 0.16 seconds, monitoring A214 and A275. A gradient of 10% acetonitrile/ 0.2% trifluoroacetic acid and 90% acetonitrile/0.2% trifluoroacetic acid were used. Peak controlled spectra were stored from 190-400 nm. Serial dilutions of IgF-1 stock material in 100 mM acetic acid were used as standard (1.875 mg/mL to 0.029 mg/mL).

Preparation of pelleted IgF-1 was as follows. A 100 µL aliquot of suspension was centrifuged at 2000 rpm for 10 minutes. 1.00 mL of 87.5% IPA/12.5% 2N HCl was added to the pellet and incubated on ice for 45 minutes. 200 µL of 1M Tris solution, pH 9 was added and the mixture was vortexed again. The sample was microfuged at 14,000 rpm for 2 minutes. 200 µL of sample was added to 800 µL 10% acetonitrile/0.2% trifluoroacetic acid in an HPLC vial and put on the HPLC column. The supernatant from the pellet was diluted 5- or 10-fold using 10% acetonitrile/0.2% trifluoroacetic acid and placed in an HPLC vial and put on the HPLC column.

For determination of free amikacin in the supernatant, the suspension was centrifuged at 800 g for 3 minutes using a Sorvall RT-6000B. 40 µL of the supernatant were added to 30 µL of normal saline and 150 µL IPA, vortexed gently and incubated at 55° C. for one hour. For determination of total amikacin in the suspension, samples were diluted 1:10 in normal saline and vortexed thoroughly. This solution was diluted 1:4 in IPA and vortexed gently and then incubated at 55° C. for one hour. The samples of blown down second emulsion in sucrose-lysine were washed in saline and analyzed using a Particle Concentration Fluorescence Immunoassay (PCFIA). 1 mL of 123 mM phosphate buffer, pH 7.4 was added to each sample preparation and vortexed thoroughly. 15 µL of each sample was then added to a glass culture tube containing 3 mL of 123 mM phosphate buffer, pH 7.4. Polystyrene beads were coated with anti-amikacin antibody (The Binding Site, San Diego, Calif.) and incubated with a combination of fluorescent-labeled amikacin (The Binding Site) and amikacin-containing analyte. The amount of fluorescent-labeled amikacin bound to the beads was measured with a Fluorescence Concentration Analyzer (FCA), with 485/535 nm signal, and 590/620 nm reference signal.

Power input (kg m³/s) into a static mixer can be expressed as the linear velocity times the pressure drop.

$$\text{Power} = (\text{linear flow rate through mixer}) * (\text{pressure drop across mixer}) \quad (2)$$

Figure 14:
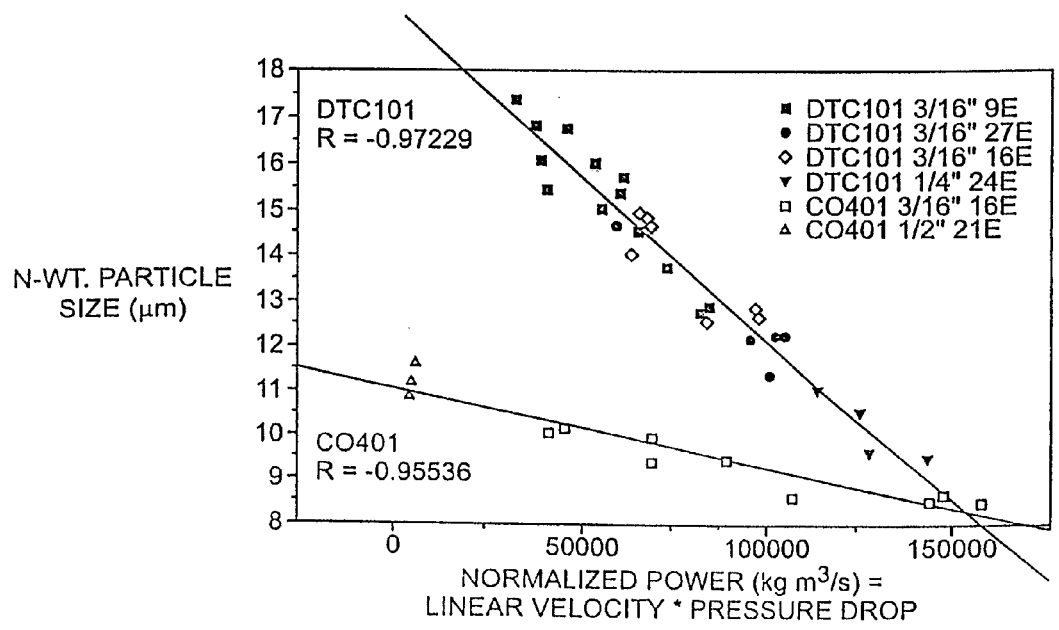
FIG. 14 is a graph showing the effect of normalized power input into static mixers of various sizes and configurations on the particle size of cytarabine- and morphine-containing preparations prepared at the 0.2 L scale.

Normalized power is obtained by dividing power by the cross sectional area of the static mixer pipe. The variation of the resulting cytarabine- and morphine-containing particle sizes with normalized power input into a static mixer is shown graphically in FIG. 14. As shown in FIG. 14, the slope of the line for the cytarabine product is steeper than that for the morphine preparation. This reflects the increased barrier to particle formation for the cytarabine preparation. The morphine preparation, in contrast, shows a low activation energy for particle formation. This trend was observed regardless of the static mixer length. Variation in the volume ratio of the first emulsion to the second aqueous phase did not have a significant effect on either the particle size or encapsulation efficiency.

The particle size-normalized power correlation for an emulsion system is a very useful tool for the scale-up of a static mixer. For a given particle size, one can obtain the normalized power from FIG. 14. Then, for a given flow rate, one can calculate the pressure drop for various static mixer diameters using the expression for power input given in Equation 2. It is clear from FIG. 14 that the particle size-power correlation is specific for a particular emulsion system. For particles of the same size, less power is required to emulsify the morphine-containing formulation than the cytarabine-containing formulation.

The Koch mixer was selected to compare with the Kenics™ mixer. The Koch mixer contains rigid mixing elements made of corrugated stainless steel sheets welded together. One element is inserted at a 90° offset from the next element. The Koch mixer used here had 5 elements and an inner diameter of 9.5 mm. Due to the larger cross-sectional area, higher flow rates were needed to match the linear velocities obtained using the Kenics™ mixer. Increasing linear velocity reduced the number and volume weighted particle sizes. The data suggested that the Koch mixer mixes more efficiently than the Kenics™ mixer, since lower linear velocities and pressure drops produced particles of the same size. However, both mixers produced similar emulsions with respect to encapsulation efficiency.

Example 7

Stability Studies

In order to determine shelf life, stability studies were performed at normal storage (4° C.) and high temperature (37° C.) conditions. The temperature of 37° C. was used to accelerate destabilization as a parameter to assess the inventive process. The purpose of accelerated stability studies was to evaluate process parameter in a more timely manner than would be possible at the lower temperature. The final material after diafiltration and adjustment to the product specific concentration was filled into vials containing 2 mL or 5 mL each. Half of these vials were held at 4° C. and half held at 37° C. A vial from each temperature was pulled periodically and analyzed for Lipocrit, total drug concentration and free drug concentration. The accelerated shelf life at 37° C. is the time period until only 90% of the total drug originally encapsulated remains encapsulated. Typical unencapsulated drug concentrations at time zero are approximately 0.01% to about 2.00%.

Example 8

Effect of Mixer Length, Mixer Size and Linear Velocity on Particle Size and Encapsulation Efficiency Particle size and encapsulation efficiency were measured as a function of static mixer length and linear velocity. FIG. 15 shows the effect of linear velocity on the size of cytarabine-containing particles created with a 3/16" Kenics static mixer with various lengths and a ¼" Kenics mixer. It can be seen that increasing linear velocity causes a decrease in particle size. The data suggest that there is an effect of mixer length on the mean particle size, that is, the shorter, 9 element mixer creates particles equal to, or larger than the 16 element mixer, while the particles made with the 27 element mixer are approximately 1-2 µm smaller. This effect may indicate that the emulsification step in the static mixer has not yet reached equilibrium and appears to be the function of the emulsion residence time in the mixer. Increasing the number of elements results in an increase in the residence time. An equilibrium particle size may be reached upon extending the residence time at a given linear velocity.

Figure 16:
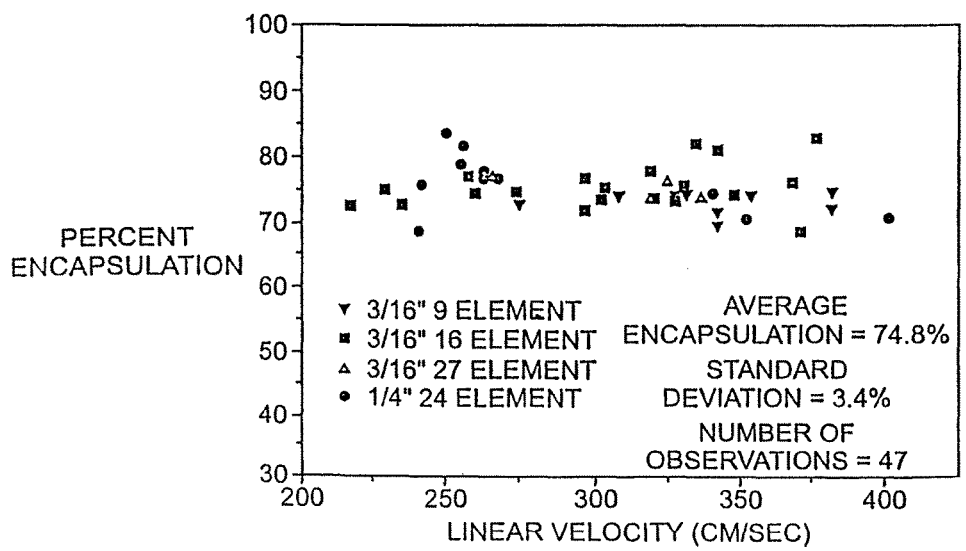
FIG. 16 is a graph showing the effect of linear velocity through static mixers of various sizes and configurations on the encapsulation efficiency of cytarabine-containing preparations prepared at the 0.2 L scale.

The effect of mixer diameter at various linear velocities on the particle size and encapsulation efficiency of the second emulsion mixing in cytarabine preparations was determined to assess the scalability of the process. FIG. 16 shows the data for the effect on encapsulation efficiency of various linear velocities using a ¼" Kenics mixer, and the 3/16" mixers of various lengths as described for the particle size determinations above. The encapsulation efficiency varies between 70% and 80% for all three mixers. The average % encapsulation for all mixers is about 74.8% with a 3.4% standard deviation. The encapsulation efficiencies for the individual Kenics™ mixers are summarized in Table 1. The encapsulation efficiencies were determined in samples after blow down.

TABLE 1

Average Encapsulation Efficiencies for Kenics ™ Static Mixers

| mixer dimensions | avg % encapsulation (std. dev.) | # of observations |
| --- | --- | --- |
| 3/16", 9 elements | 72.8 (1.7) | 8 |
| 3/16", 16 elements | 75.2 (3.4) | 22 |
| 3/16", 27 elements | 74.6 (1.5) | 5 |
| ¼", 24 elements | 75.7 (4.4) | 12 |
| overall | 74.8 (3.4) | 47 |

The data suggest that the encapsulation efficiency is independent of linear velocity and mixer length of the same mixer design.

Example 9

Effect of Temperature on the Second Emulsion Mixing

Figure 17:
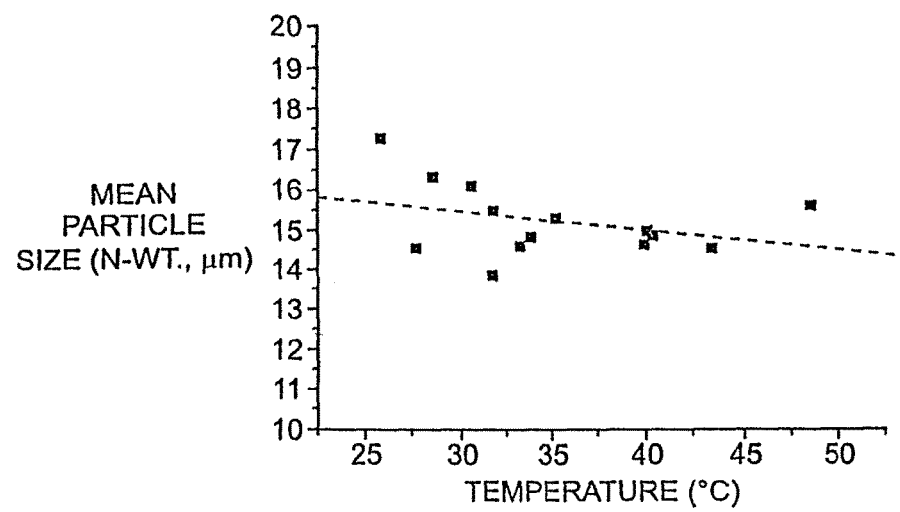
FIG. 17 is a graph showing the effect of temperature on the mean particle size of cytarabine second emulsion processed through a 3/16" Kenics static mixer equipped with 16 mixing elements.
Figure 18:
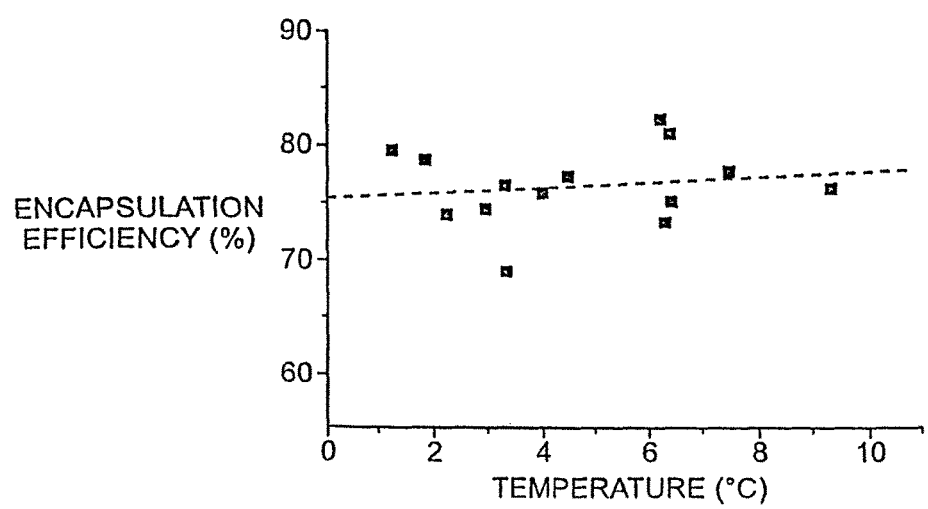
FIG. 18 is a graph showing the effect of temperature on the encapsulation efficiency of cytarabine second emulsion processed through a 3/16" Kenics static mixer equipped with 16 mixing elements.

Measurements were made to study the effect of temperature on second emulsion mixing of a cytarabine preparation as described in Example 1. The temperature range studied was between 25° C. and 47° C. For this set of experiments, the 3/16" Kenics mixer containing 16 mixing elements was used. The glucose-lysine solution was supplied using the positive displacement pump at a total constant flow rate of 1740 mL/minute. Second emulsion samples were removed for blow down and analysis. FIG. 17 shows that the effect of temperature on the mean number weighted particle size is not significant and it is very minor. FIG. 18 shows that there is no effect of changes in temperature on encapsulation efficiency.

Example 10

Reproducibility of Second Emulsion Mixing Using Static Mixers

The reproducibility of second emulsion of a cytarabine preparation as described in Example 1 using a static mixer was evaluated. The cytarabine first emulsion from the bench scale (100 mL) system was emulsified with a glucose-lysine second aqueous solution as described above in Example 2 using a 3/16" Kenics static mixer (16 elements) using a flow rate of about 1750 mL/min. The flow rate corresponds to a linear velocity of approximately 330 cm/sec. The glucose-lysine temperature was held constant at 40° C., and the volumetric ratio of the streams was 1:5.67 (first emulsion: glu-Lys). Samples were blown down and analyzed for particle size (number weighted) and encapsulation efficiency. The data for individual runs are shown in Table 2.

TABLE 2

Reproducibility of Second Emulsion Using Static Mixers

| Flow Rate (mL/min) | % Encapsulation | Mean particle size (µm) |
| --- | --- | --- |
| 1750 | 80.0 | 15.3 |
| 1740 | 75.0 | 14.9 |
| 1740 | 78.5 | 14.5 |

TABLE 2-continued

Reproducibility of Second Emulsion Using Static Mixers

| Flow Rate (mL/min) | % Encapsulation | Mean particle size (μm) |
|---|---|---|
| 1776 | 75.7 | 14.8 |
| 1740 | 77.1 | 15.2 |
| Average | 77.3 | 14.95 |
| Standard Deviation | 2.0 | 0.34 |
| RSTD | 3% | 2% |

The data demonstrate that both particle size and % encapsulation are very reproducible.

The reproducibility study set forth above was repeated using morphine-containing first emulsion, prepared as described above in Example 5. Number-weighted particle size varied with mixer linear velocity (correlation $R^2=0.857$), and resulted in smaller particle sizes than with cytarabine (about 9.5 μm, vs. about 15 μm with cytarabine at 350 cm/sec). The encapsulation efficiency varied between 78% and 87%, and was independent of linear velocity.

Four batches of morphine-containing MVL were prepared at the 1 L scale using the static mixer for second emulsification. The first emulsion was prepared as described as above. One batch was prepared using a ¼" static mixer. However, the low linear velocity required for morphine-containing formulations resulted in a process time of over 10 minutes, so a ½" OD mixer was used for the remaining three batches. The results are shown in Table 3 below.

TABLE 3

Effect of Static Mixer Size on Product Parameters

| Analyses | ¼" static mixer | ½" static mixer |
|---|---|---|
| Mean particle size, prior to cross-flow (μm) | 11.3 (0% ≤ 5 μm) | 11.18 (0% ≤ 5 μm) |
| Mean particle size, after cross-flow (μm) | NA | 11.63 (0% ≤ 5 μm) |
| Encapsulation efficiency (%) | 68.6 | 67.8 |

The results demonstrated that the mean particle size and encapsulation efficiency after sparge are comparable for the two mixers. All batches met the post cross flow particle size specification of 0% particles at ≤5 μm. Thus, the static mixer provides a highly reproducible product at commercial scale. Accelerated stability of the three samples which went through the ½" mixer showed that all batches were stable for at least 20 days at 37° C., with some samples exceeding 27 days.

Example 11

Permeate Back Pulsing in Primary Filtration

Backward pulsation of permeate is a method to reduce or disrupt the gel polarization layer during diafiltration with a hollow fiber filter. This can increase the efficiency of a cross-flow filtration system with respect to permeate flux, total membrane surface area and process time. Crossflow was conducted to allow for quicker batch turn-around, more replicates and less material consumption. The process parameters were scaled down 20-fold from a larger scale process. The diafiltration used in this example consisted of three steps: initial concentration, buffer concentration, and final concentration. The retentate flow is kept constant during initial concentration and buffer exchange. During the final concentration, the flow is reduced by 40%. The effect on the flux is a sudden drop at this stage of the crossflow. This normal and expected change allows for less shear force on the MVL particles. All permeate flux data was corrected to 20° C. Comparison of the scale-down data indicates that the permeate flux profiles at both scales are in good agreement, and are used as a control.

Figure 19:
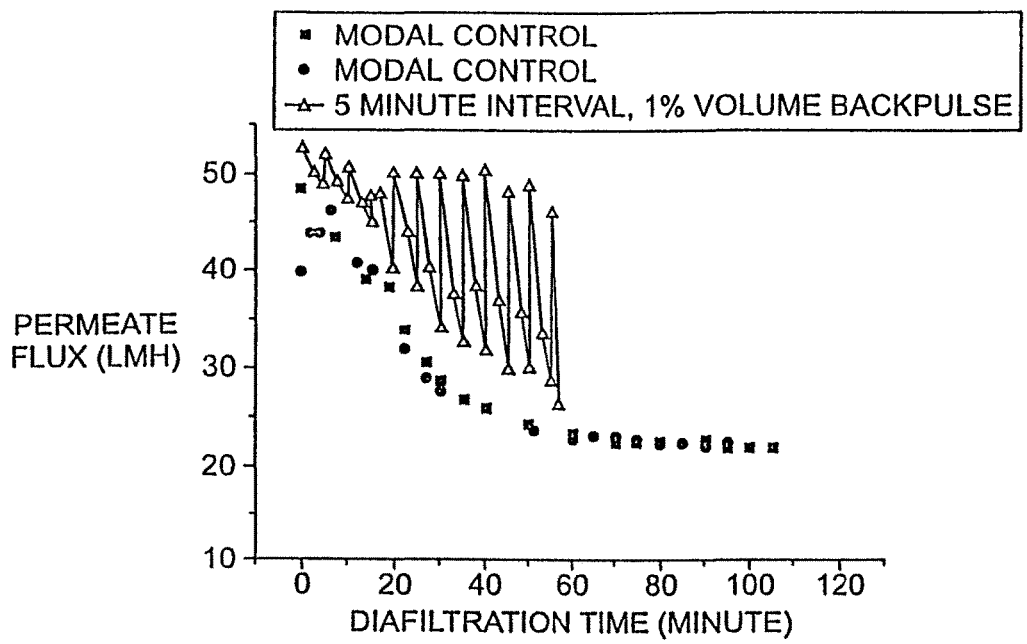
FIG. 19 is a graph showing the effect of 1% volume back pulsing the retentate flow every 5 minutes on the permeate flux of a cytarabine MVL preparation.

The effect of back pulsing was determined as follows. During a cross-flow filtration with no permeate pump, the permeate flux typically decreases shortly after the start of the process. This decrease is caused by the combination of two effects: the onset of the gel polarization layer and membrane fouling. By periodically reversing the permeate flow to back pulse with either permeate or any other aqueous solution, the permeate flux recovers to its initial level. This increases the average permeate flux and therefore, decreases the overall process time significantly. The drop in permeate flux at approximately 60 minutes for the batch with back pulse is due to the reduction in retentate speed. These effects are seen in FIG. 19. For this measurement, approximately 4-5 psig back pressure was applied to the retentate line during cross-flow filtration. The back pulse was conducted with 10-12 psig on the back pulse line.

Figure 20:
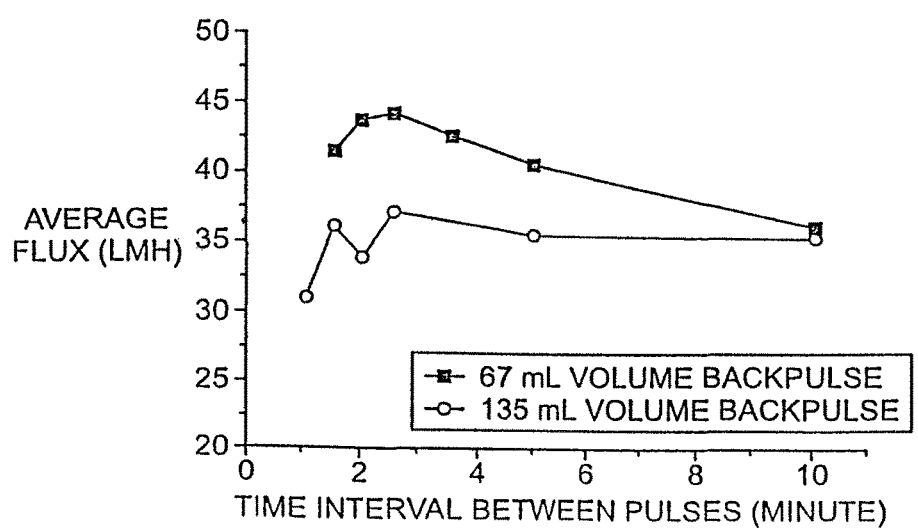
FIG. 20 is a graph showing the effect of varying the back pulse time interval from 1 to 10 minutes for back pulse volumes of 67 mL and 135 mL on the permeate flux of a cytarabine preparation.

The diafiltration was further evaluated by varying the interval between pulses for two back pulse volumes, 67 mL and 135 mL (0.2x system). The results are shown in FIG. 20. The back pulse volume is directly proportional to the duration of the back pulse at constant transmembrane pressure (TMP). Reducing the time interval from 10 minutes between pulses increases the average flux until about three minute interval is reached. At intervals greater than about 2.5 minutes, the benefits of back pulsing are outweighed by the disadvantage of the additional volume to be removed. At shorter intervals, the average flux is reduced because the back pulse volume is pumped repetitively.

Figure 21:
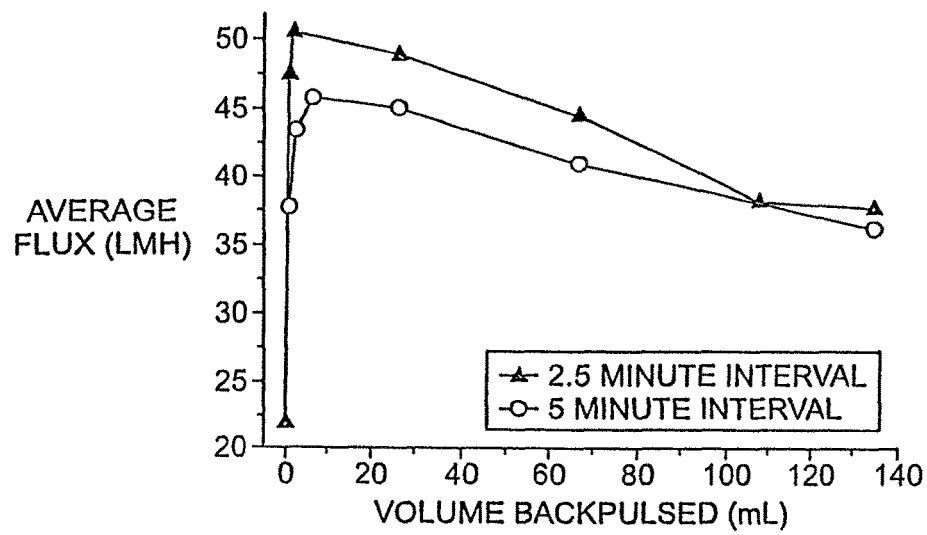
FIG. 21 is a graph showing the effect of varying the back pulse volume from 0 to 140 mL for back pulse intervals of 2.5 and 5 minutes on the permeate flux of a cytarabine MVL preparation.

The effect of the back pulse volume on the process time was evaluated at constant intervals of 2.5 and 5 minutes. FIG. 21 shows that there is an optimum back pulse volume for each interval 2.7 mL and 27 mL. At back pulse volumes below the optimum, there is a steep decline, indicating that the back pulse volume is insufficient to lift off the gel polarization layer completely. A back pulse experiment was performed where no back pulse volume was used, but the permeate valve would shut for 2 seconds (average time required to back pulse 67 mL). The flux recovery was poor, demonstrating that it is the back pulse of the fluid, not the intermittent interruption of the permeate flow that removes the gel layer. At higher volumes than the optimum, the flux declines nearly linearly due to excessive back pulse volume.

Table 4 displays the effect of diafiltration on process times for various intervals between pulses, using various back pulse volumes.

TABLE 4

Effect of Back Pulsing Diafiltration on Process Times

| Interval between pulses (minutes) | Back pulse volume (mL) | Time savings for diafiltration (%) |
|---|---|---|
| 2 | 67.5 | 40 |
| 2.5 | 67.5 | 37 |
| 5 | 2.7 | 34 |
| 5 | 6.75 | 38 |
| 5 | 27 | 36.5 |
| 2.5 | 2.7 | 44 |
| 2.5 | 27 | 41.5 |
| 2.5 | 67.5 | 41.5 |
| 2.5 | 94.5 | 33 |

These data show that long intervals between back pulses and small back pulse durations (that is, small back pulse volumes) can cause incomplete permeate flux recovery. Further, there is an optimum interval between back pulses and back pulse volume to maximize the permeate flux, thereby reducing the process time of a diafiltration process. For the system tested, the maximum time savings achieved using back pulsing was 44%.

Example 12

Automated Back Pulsing Diafiltration

Special equipment responsive to a proprietary computer program was installed for the automation of back pulse experiments. Automation enabled testing of smaller back pulse volumes (down to 0.1% volume back pulse stream, or 2.7 mL) and various back pulse intervals (as short as 1 minute). Automating the back pulse process also increased the accuracy of step increases in back pulse volume because the volume is determined on a millisecond time scale and involves no human reaction time before the valves are adjusted. As a part of the automation process, a flow meter was installed and coupled to the computer. The flow meter provided an instant representation of the flow, rather than an average over a minute, as is the case for manual back pulsing.

It has been consistently found that the process time is significantly decreased with the use of automation for all sets of process parameters tested. For example, when a two minute interval was used with a 2.5% volume back pulse, the manual average process time was 85.9 minutes (standard deviation 6.7 minutes, 6 measurements). The comparable automated run was completed in 60 minutes. An additional advantage of automating the back pulsing process is that a more accurate representation of the gel layer formation and removal can be graphed.

Example 13

Secondary Cross-Flow Filtration

Pre-adjustment bulk material from a cytarabine preparation was prepared at the 10 L scale following standard procedures as described above. Non-sterile batches were made using the 10 L equipment performing the following cycles: first emulsion, second emulsion, sparge, cross-flow diafiltration including a priming step, and clean-in-place (CIP) circuit A and B.

The post primary filtration material from a cytarabine preparation as described above in Example 1 (approximately 32 kg) was further concentrated using a secondary cross-flow filtration system. The cross-flow module was a 0.2μ AGT module (A/G Technology), catalog # CFP-2-E-55. The bulk was contained in the 10 L product vessel. The retentate was recirculated using a 700 series Watson Marlow pump while monitoring the retentate weight using the floor scale. Permeate was monitored manually, and with an EG&G turbine flow meter. Retentate inlet, retentate outlet and permeate pressures were monitored to determine the transmembrane pressure (TMP). In some experiments, back pressure was applied to the return line monitoring the pressure increase on the inlet pressure.

The effect of the wall shear rate (that is, retentate speed), transmembrane pressure, and initial permeate rate on the process time and yield were determined. Five batches were run under exactly the same conditions to determine the variability. A linear correlation between total cytarabine concentration and the final volume of material after secondary cross-flow filtration was found. Thus, the amount of cytarabine passing through the membrane is negligible.

The average concentration for all batches combined was 10.4 mg/mL (0.6 mg/mL standard deviation). The step yield for adjustment by secondary cross-flow filtration was 96.9% (standard deviation of 2.7%), while the step yield for adjustment by decanting was 92.8% (standard deviation 3.4%). Thus, there is an 8.4% improvement in overall yield associated with the use of secondary cross-flow filtration as an adjustment step.

Example 14

The Effect of Retentate Speed on Process Time and Yield

The effect of retentate speed in secondary filtration on process time and yield was determined for retentate speeds between 6 Lpm and 10 Lpm, and is shown in Table 5.

TABLE 5

Effect of Retentate Speed on Process Parameters.

| | retentate speed (Liters/minute) | time (minutes) | cross-flow yield |
|---|---|---|---|
| "control" | 8 | 50 | 94.5% |
| "control" | 8 | 50 | 97.2% |
| reduce retentate | 7.1 | 47 | 98.1% |
| reduce retentate | 6 | 51 | 95.7% |
| increase retentate | 10 | 50 | 95.1% |

No back pressure was applied to the retentate stream, and the permeate flux was not controlled. Table 5 shows that there is virtually no effect on process parameters arising from changes in retentate speed between these values.

Example 15

Effect of Transmembrane Pressure on Process Parameters

The effect of transmembrane pressure (TMP) in secondary filtration on process time and yield were evaluated at two different retentate speeds, 8 lpm and 6 lpm. When applying no back pressure on the retentate line, the initial TMP is about 0.7 psi to about 0.9 psi. This TMP was compared to an increase of approximately 1 psi. The data in Table 6 suggest that the process yield was not affected by the changes in TMP.

TABLE 6

Effect of Transmembrane Pressure on Process Yield

| flow rate | initial TMP (psi) | Yield (%) |
|---|---|---|
| 8 lpm | 0.9 | 94.5 |
| 8 lpm | 0.85 | 97.2 |
| 8 lpm | 1.6 | 104.2 |
| 8 lpm | 1.5 | 95.5 |
| 6 lpm | 0.7 | 95.7 |
| 6 lpm | 1.4 | 101.0 |
| 6 lpm | 1.6 | 98.6 |

Figure 22:
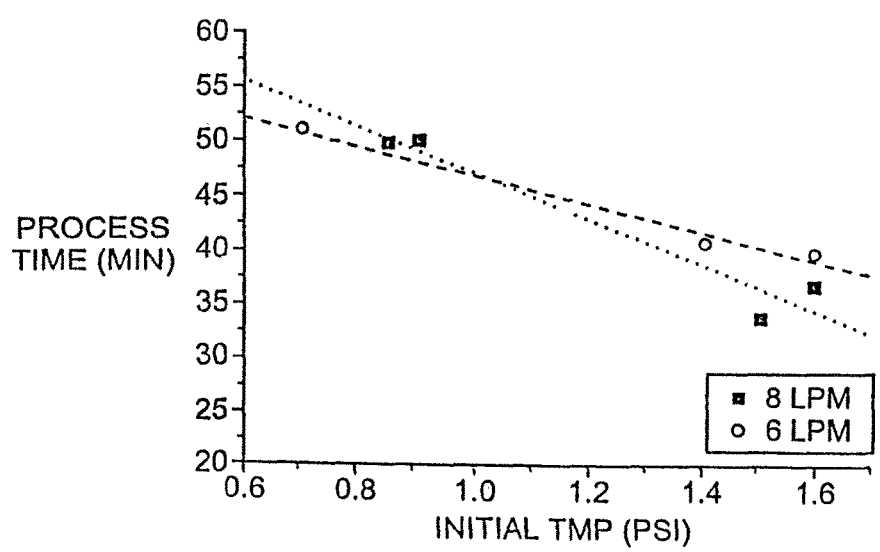
FIG. 22 is a graph showing the effect of transmembrane pressure on the process time at two different retentate speeds, 6 lpm and 8 lpm.

However, there is a significant reduction in process time for both retentate speeds as shown in FIG. 22. The process time could be reduced from approximately 50 minutes to as low as about 35 minutes by applying a 1.5 to 1.6 psi TMP corresponding to an inlet pressure increase of 3 psig.

Example 16

Release Specifications of Secondary Cross-Flow Filtration

Five batches which were prepared at constant process parameters, and two other batches were tested extensively for release specifications. The product tests were lipid content in vitro release testing and 2-8° C. shelf life. The conclusion is that the presence of fines in the product prepared with secondary cross-flow filtration (and which are removed from the product in the decanting process step) do not negatively affect the product properties in vitro.

Example 17

1 L to 25 L Scale Production Specification Comparison

The morphine-containing product produced by both the 1 L and 25 L processes of the invention was compared. The secondary emulsification was carried out with a shear mixer as specified in Example 2. The product specification results are presented in Table 7.

TABLE 7

Product Specification Comparison

| Product Specification | 1 L | 25 L |
| --- | --- | --- |
| Particle Size (microns) | 16.3 | 15.5 |
| Percent Free Morphine (%) | 1.4 | 1.4 |
| Total Morphine (g/L) | 10.4 | 10.5 |
| Percent Encapsulated (%) | 46 | 41 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed:

1. A process for preparing a multivesicular liposomal particle composition of pre-determined, uniform size distribution, the process comprising:
  a) providing a first emulsion by mixing a first aqueous phase and a volatile water-immiscible solvent phase, said solvent phase comprising at least one amphipathic lipid and at least one neutral lipid;
  b) mixing and emulsifying said first emulsion and a second aqueous phase in a mixer to provide a second emulsion, said second emulsion comprising a continuous aqueous phase;
  c) sparging the volatile water-immiscible solvent from the second emulsion to form an aqueous suspension of multivesicular liposomal particles by bubbling an inert gas through the second emulsion using at least one sparge ring, at least one sparge tube or at least one frit;
  d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm;
  e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions,
  f) the composition is prepared in quantities or batches greater than a liter; wherein the first emulsion is mixed in a first emulsification vessel of at least 10 liters in volume; and
  g) wherein the uniform size distribution has a number weighted mean particle size of at least 10 microns.

2. The process of claim 1, wherein the sparging comprises at least two steps having different flow rates.

3. The process of claim 1, wherein the volume ratio of the first aqueous phase to the water-immiscible solvent phase is from 0.33 to 1.6.

4. The process of claim 1, wherein the volume ratio of the first emulsion to second aqueous phase is from 0.01 to 0.5.

5. The process of claim 1, wherein the volume ratio of the first aqueous phase to the water-immiscible solvent phase is from 0.33 to 1.6; and, the volume ratio of the first emulsion to second aqueous phase is from 0.01 to 0.5.

6. The process of claim 1, wherein the filter is a hollow fiber filter.

7. The process of claim 1, wherein the sparging comprises passing an inert gas through at least one sparge ring.

8. The process of claim 1, wherein the inert gas is nitrogen or argon.

9. The process of claim 6, wherein the filter has a membrane pore size from 0.1 µm to 0.2 µm.

10. The process of claim 1, wherein the first emulsification vessel further comprises a water jacket.

11. The process of claim 1, wherein the first emulsification vessel is 10 liters in volume.

12. The process of claim 1, wherein the first emulsification vessel is 20 liters in volume.

13. The process of claim 1, wherein the first emulsification vessel is 25 liters in volume.

14. The process of claim 1, wherein the first emulsification vessel is 75 liters in volume.

15. The process of claim 1, wherein the first emulsification vessel is 100 liters in volume.

16. A process for preparing a multivesicular liposomal particle composition of pre-determined, uniform size distribution, the process comprising:
  a) primary filtration by cross-flow filtration of an aqueous suspension of multivesicular liposomal particles by cross-flow filtration; and
  b) secondary filtration by cross-flow filtration of the aqueous suspension to reduce the initial volume to provide a subsequent volume of aqueous media that is 10% to 90% of the initial volume, wherein all steps are carried out under aseptic conditions.

17. The process of claim 16, where in the primary and secondary filtration is carried out with one or more hollow fiber filters.

18. The process of claim 17, wherein the one or more filters have a membrane pore size from 0.1 microns to 0.2 microns.

19. The process of claim 18, wherein the uniform size distribution has a number weighted mean particle size of at least 10 microns.

20. The process of claim 17, wherein the one or more filters are fluidly connected to a retentate vessel containing the aqueous suspension to be filtered.

21. The process of claim 20, wherein the retentate vessel is at least 10 liters in volume.

22. The process of claim 21, wherein the retentate vessel further comprises a water jacket.

23. The process of claim 21, wherein the retentate vessel is 10 liters in volume.

24. The process of claim 22, wherein the retentate vessel is 20 liters in volume.

25. The process of claim 21, wherein the retentate vessel is 25 liters in volume.

26. The process of claim 21, wherein the retentate vessel is 75 liters in volume.

27. The process of claim 21, wherein the retentate vessel is 100 liters in volume.

28. A process for preparing a multivesicular liposomal particle composition, the process comprising:
  a) providing a volume of first emulsion by mixing a volume of a first aqueous phase and a volume of a volatile water-immiscible solvent phase, said solvent phase comprising at least one amphipathic lipid and at least one neutral lipid;
  b) mixing and emulsifying said first emulsion and a volume of a second aqueous phase in a high shear mixer to provide a volume of a second emulsion, said second emulsion comprising a continuous aqueous phase; and
  c) removing the volatile water-immiscible solvent from the second emulsion to form a volume of multivesicular liposomal particle composition, wherein said solvent removal comprises contacting the second emulsion with an inert gas flow; and
  wherein said process further comprises primary filtration of the multivesicular liposomal particle composition by cross-flow filtration using a filter having a membrane where the multivesicular liposomal particle composition does not pass through the membrane;
  wherein all steps are carried out under aseptic conditions, and wherein all solutions are sterile filtered, and wherein the multivesicular liposomal particle composition is immediately suitable for administration into humans; and
  wherein the primary filtration comprises:
    a first concentration of the multivesicular liposomal particle composition; and
    a buffer exchange, resulting in a pH of the multivesicular liposomal particle composition of between about 5 and about 8, and the primary filtration is conducted at a transmembrane pressure of from about 0.1 psi to about 7 psi.

29. The process of claim 28, wherein the mixer is a dynamic or static mixer.

30. The process of claim 28, wherein the volume ratio of the first aqueous phase to the water-immiscible solvent phase is from about 0.33 to about 1.6.

31. The process of claim 28, wherein the volume ratio of the first emulsion to the second aqueous phase is from about 0.05 to about 0.5.

32. The process of claim 28, wherein the at least one amphipathic lipid is selected from the group consisting of phosphatidylcholines, phosphatidylethanolamines, sphingomyelins, lysophosphatidylcholines, lysophosphatidylethanolamines, phosphati dylglycerols, phosphatidylserines, phosphatidylinositols, phosphatidic acids, cardiolipins, acyl trimethylammonium propane, diacyl dimethylammonium propane, and ethyl phosphati dylcholine.

33. The process of claim 28, wherein the at least one neutral lipid is selected from the group consisting of glycerol esters, glycol esters, tocopherol esters, sterol esters, and squalenes.

34. The process of claim 28, wherein the filter is a hollow fiber filter.

35. The process of claim 28, further comprising potency adjustment of the multivesicular liposomal particle composition.

36. The process of claim 35, wherein the potency adjustment is carried out by secondary filtration.

37. The process of claim 28, wherein the multivesicular liposomal particle composition comprises an encapsulated physiologically active substance.

38. The process of claim 37, wherein the physiologically active substance is selected from the group consisting of antianginas, antiarrhythmics, antiasthmatic agents, antibiotics, antidiabetics, antifungals, antihistamines, antihypertensives, antiparasitics, antineoplastics, antivirals, cardiac glycosides, hormones, immunomodulators, monoclonal antibodies, neurotransmitters, nucleic acids, proteins, radio contrast agents, radionuclides, sedatives, analgesics, steroids, tranquilizers, vaccines, vasopressors, anesthetics, peptides, prodrugs and pharmaceutically acceptable salts of the same.

39. The process of claim 38, wherein the physiologically active substance is selected from cytarabine, insulin, paclitaxel, 5-fluorouracil, floxuridine, morphine, hydromorphine, dexamethasone, methotrexate, bleomycin, vincristine, vinblastine, IgF-1, bupivacaine and amikacin.

40. A process for preparing a multivesicular liposomal particle composition, the process comprising:
  a) providing a volume of first emulsion by mixing a volume of a first aqueous phase and a volume of a volatile water-immiscible solvent phase, said solvent phase comprising at least one amphipathic lipid and at least one neutral lipid;
  b) mixing and emulsifying said first emulsion and a volume of a second aqueous phase in a mixer to provide a volume of a second emulsion, said second emulsion comprising a continuous aqueous phase; and
  c) removing the volatile water-immiscible solvent from the second emulsion to form a volume of multivesicular liposomal particle composition, wherein said solvent removal comprises contacting the second emulsion with an inert gas flow; and
  wherein said process further comprises primary filtration of the multivesicular liposomal particle composition by cross-flow filtration using a filter having a membrane where the multivesicular liposomal particle composition does not pass through the membrane;
  wherein the multivesicular liposomal particle composition is sterilized before filling, and wherein the multivesicular liposomal particle composition is immediately suitable for administration into humans; and
  wherein the primary filtration comprises:
    a first concentration of the multivesicular liposomal particle composition; and
    a buffer exchange, resulting in a pH of the multivesicular liposomal particle composition of between about 5 and about 8, and the primary filtration is conducted at a transmembrane pressure of from about 0.1 psi to about 7 psi.

41. A multivesicular liposomal particle composition made by the process of claim 28.

42. The process of claim 35, wherein the volume of multivesicular liposomal particle composition is pooled and further processed by multiple batch processing.

43. The process of claim 28, wherein the membrane is rated at 0.2 μm.

* * * * *